US006385589B1

(12) United States Patent
Trusheim et al.

(10) Patent No.: US 6,385,589 B1
(45) Date of Patent: May 7, 2002

(54) SYSTEM FOR MONITORING AND MANAGING THE HEALTH CARE OF A PATIENT POPULATION

(75) Inventors: Mark Trusheim, Chesterfield, MO (US); Ann McAlearney, Worthington, OH (US); Timothy Melkus; J. Michael Yager, both of Chicago, IL (US)

(73) Assignee: Pharmacia Corporation, Skokie, IL (US)

( * ) Notice: Subject to any disclaimer, the term of this patent is extended or adjusted under 35 U.S.C. 154(b) by 0 days.

(21) Appl. No.: 09/223,022

(22) Filed: Dec. 30, 1998

(51) Int. Cl.[7] .............................................. G06F 17/60
(52) U.S. Cl. ................................................. 705/2; 705/3
(58) Field of Search ........................................ 705/2, 3

(56) References Cited

U.S. PATENT DOCUMENTS

| | | | |
|---|---|---|---|
| 4,130,881 A | 12/1978 | Haessler et al. ............. 364/900 |
| 4,679,144 A | 7/1987 | Cox et al. .................... 364/417 |
| 4,878,175 A | 10/1989 | Norden-Paul et al. . 364/413.01 |
| 5,072,383 A | 12/1991 | Brimm et al. ............ 364/413.02 |
| 5,077,666 A | 12/1991 | Brimm et al. ........... 364/413.02 |
| 5,301,105 A | 4/1994 | Cummings, Jr. ............. 364/401 |
| 5,346,480 A | 9/1994 | Hess et al. ................... 604/197 |
| 5,471,382 A | 11/1995 | Tallman et al. ............. 364/406 |
| 5,517,405 A | 5/1996 | McAndrew et al. ......... 364/401 |
| 5,557,514 A | 9/1996 | Seare et al. .................. 364/401 |
| 5,583,758 A | 12/1996 | McIlroy et al. ............. 395/202 |
| 5,832,448 A * | 11/1998 | Brown ........................... 705/2 |
| 6,148,297 A * | 11/2000 | Swor et al. ..................... 707/3 |

FOREIGN PATENT DOCUMENTS

| WO | 97/15019 | 4/1997 | ........... G06F/19/00 |
| WO | 97/15021 | 4/1997 | ........... G06F/19/00 |
| WO | 97/15022 | 4/1997 | ........... G06F/19/00 |

* cited by examiner

Primary Examiner—Richard Chilcot
Assistant Examiner—J Harle
(74) Attorney, Agent, or Firm—Fitzpatrick, Cella, Harper & Scinto

(57) ABSTRACT

A system for managing the health care of a plurality of members in a population includes identification of member characteristics of one of the plurality of members, storage of a list of the member characteristics, continuous monitoring for information indicative of a medical event, obtaining information indicative of a medical event, automatic identification of a risk situation based on the member characteristics of the one member and the medical event, generation of a notification to address the risk situation, the notification being associated with a predetermined script to address the identified risk situation. Preferably, the risk situation corresponds to a potential process failure in the delivery of health care to the member.

24 Claims, 41 Drawing Sheets

UniHealth/Monsanto

Welcome to VIHMS

*"Virtually Integrated Health Management System"*

100

User Name: _____ —102

Password: 105 _____ —104

[Sign In]   [Clear]

FIG. 18

Notification Details

○ *HOSPITAL ADMISSION* ○

Member Name ⇨

*FLORENCE ELISE MELIN*

Admit Date: 07/21/98
Diagnosis Description: PNEUMONIA
Hospital Name: NHSWC (ADT)
Last Update: 07/21/98

Main Menu

Member Look-Up
Transfer Member
Demographics
Eligibility
Notifications
Coordination Plan
Summary
Assessments
Resources
Provider Referral
Help
Change Password

Eligibility

Member: 900000000000 VICTORIA JO KLINE
Member Address: 5449 HAXELTINE STREET
SHERMAN OAKS, CA 910422212
Phone: (818) 454-4545

PCP:
Phone: 0-

Current Information

Source: CareAmerica
Medicare Number: 8888F8F6888
MediCal Number:
IPA: VERDUGO
PCP Effective Date: 09/01/1997
Plan Name: NoDescription
Eligibility Start Date: 09/01/1997
Eligibility End Date:

Prior Information

PCP:
Effective Date:

---

Main Menu

Member Look-Up
Transfer Member
Demographics
Eligibility
Notifications
Coordination Plan
Summary
Assessments
Resources
Member Profile
Provider Referral
Help
Change Password

FIG. 19

```
Main
Menu

Member
Look-Up
Transfer
Member
Demographics
Eligibility
Notifications
Coordination
Plan
Summary
Assessments
Resources
Member
Profile
Provider
Referral
Help
Change
Password
```

Demographics ⟵ 120                                    Site Code: 9900

Member:900000000006 — THOMAS J LIMONES
Medicare:8888H8H798H

Phone: (818) 999-9555
Work Phone:

Member Address:
  808 MICHAEL DRIVE
  ENCINO , CA 913333345

(DOB):20-Jun-1921          Age:77        Sex:MALE        Vihms Eligible ☐
                                                         Survey ☑  09/18/1998

PCP:   SIDNEY G WHITE                                    Marital Status:

Phone: (818) 340-8080                                    Specialty:
                                                         IPA NHRC
D.O.D.            Decreased ☐
Demographic Update ☑
ALA ☐             Delegated ☐           Disenrolled ☐
SNF ☑

Edit Demographics ⟵ 122

FIG. 20

Edit Demographics

Member:90000000006 - THOMAS J LIMONES
Site Code:9900
Medicare:8888H8H798H

Phone: (818) 999-9555
Work Phone:

Member Address:
808 MICHAEL DRIVE
ENCINO , CA 913333345

(DOB):20-Jun-1921        Age:77        Sex:MALE

PCP: SIDNEY G WHITE
Phone: (818) 340-8080

Vihms Eligible ☐
Survey ☑  09/18/1998

Marital Status:

Specialty:

IPA NHRC

Member Name:
Member ID: 90000000006
Medicare: 8888H8H798H
Address:

Main Menu
Member Look-Up
Transfer Member
Demographics
Eligibility
Notifications
Coordination Plan
Summary
Assessments
Resources
Member Profile
Provider Referral
Help
Change Password

FIG. 21

Edit Demographics

Member: 900000000006 - THOMAS J LIMONES  PCP: SIDNEY G WHITE
Member Address: 808 MICHAEL DRIVE
ENCINO, CA 913333345  Phone: (818) 340-8080
Phone: (818) 999-9555

Diagnosis  Clinical Alerts: No  Delegated: No
CAD
HYPERTENSION
OSTEOARTHRITIS

No Caregiver Info

Problems  Goals
Home health services not ordered  Obtains timely home health services
Lab tests not routinely done to monitor med(s)  Schedules routine lab tests to monitor med(s)
Lacks an appropriate plan for coverage  Demonstrates knowledge-coverage plan
Lacks an appropriate plan for coverage  Develops a plan for coverage
  More Goals Last completed intervention: 11/24/1998
Intervention in process
No community resource is completed
No community resource is in process No Follow-Up Notifications Comments:
Quadruple bypass scheduled for 1/3/99

Main Menu
Member Look-Up
Transfer Member
Demographics
Eligibility
Notifications
Coordination Plan
Summary
Assessments
Resources
Member Profile
Provider Referral
Help
Change Password

Intervention History

Member: 1000010266 – FLORENCE ELISE MELIN  
Phone: (626) 777-7777  
PCP: LUKE CHAN  
Phone: (909)985-7211

| VARIANCE | Intervention | Time | Barrier | Completion Date | UNDO |
|---|---|---|---|---|---|
| | Other details | | | | |
| 08A2 | Hospitalization Assessment. | 15 | None | 07/21/98 11:39:25 | O |
| 09A3 | Confirm that physician(s) have copy of DPAHC form. | 0 | None | 07/21/98 09:10:04 | O |
| 09A2 | Provide education or counseling. | 0 | None | 07/21/98 09:09:52 | O |
| 09A1 | Determine DPAHC status. | 0 | None | 07/21/98 09:09:42 | O |
| 09A | *Durable Power of Attorney for Health Care:* | 0 | None | 07/21/98 09:09:28 | O |
| 05A1 | Functional Status and Economic Assessments. | 0 | None | 07/21/98 09:09:08 | O |
| 19A4 | Advise the member in the use of the mail order pharmacy. | 0 | None | 07/20/98 16:13:53 | O |
| 19A3 | Advise member to bring medications to next PCP appointment. | 0 | None | 07/20/98 16:13:46 | |
| 19A1 | Medication Management assessment. | 0 | None | 07/20/98 16:13:37 | O |
| 10C3 | Provide education materials. | 0 | None | 07/20/98 16:13:01 | O |
| 10C2 | Provide education or counseling. | 0 | None | 07/20/98 16:12:56 | O |
| 09A3 | Confirm that physician(s) have copy of DPAHC form. | 0 | None | 07/20/98 16:12:50 | O |
| 09A2 | Provide education or counseling | 0 | None | 07/20/98 16:12:45 | O |
| 09A1 | Determine DPAHC status. | 0 | None | 07/20/98 16:12:39 | O |
| 09A | *Durable Power of Attorney for Health Care:* | 0 | None | 07/20/98 16:12:29 | O |
| 08B3 | Follow-up with provider of agency. | 0 | None | 07/20/98 16:12:23 | O |
| 08B2 | Confirm/monitor services. | 0 | None | 07/20/98 16:12:17 | O |
| 05A4 | Confirm/monitor services received. | 0 | None | 07/20/98 16:12:09 | O |

Coordination Plan
Intervention Summary
Intervention History
Intervention Details
Member Characteristics
Send Summary Report
Send Letter
Schedule Follow Up
Resources
Create SOP
Assessments
Notepad
Summary
Main Menu

Claims

Member: 10000010266 - FLORENCE ELISE MELIN
Phone: (626) 777-7777

PCP: LUKE CHAN
Phone: (909)985-7211

Searching...
Done.

| Source | Claim Number | Service Date | Place of Service | Encounter Reason |
|---|---|---|---|---|
| HPG | 01109866 | 05/15/98 | Office | 01 |
| Diagnosis 1 | Diagnosis 2 | Diagnosis 3 | Provider Name | Provider Speciality |
| 250.00 | 272.1 | | JAMES STEWART | PCP INTERNAL MEDICINE |
| Source | Claim Number | Service Date | Place of Service | Encounter Reason |
| HPG | 01237005 | 06/15/98 | Office | 01 |
| Diagnosis 1 | Diagnosis 2 | Diagnosis 3 | Provider Name | Provider Speciality |
| 250.00 | 272.1 | | JAMES STEWART | PCP INTERNAL MEDICINE |
| Source | Claim Number | Service Date | Place of Service | Encounter Reason |
| HPG | 01237143 | 06/15/98 | Office | 01 |
| Diagnosis 1 | Diagnosis 2 | Diagnosis 3 | Provider Name | Provider Speciality |
| 250.00 | 272.1 | | JAMES STEWART | PCP INTERNAL MEDICINE |
| Source | Claim Number | Service Date | Place of Service | Encounter Reason |
| HPG | 01237147 | 06/15/98 | Office | 01 |

Summary
Claims
Encounters
Medications
Authorizations
Test Results
Clinical Alerts
Main Menu

FIG. 30

Medications

Member: 100000110266 - FLORENCE ELISE MELIN  
Phone: (626) 777-7777

PCP: LUKE CHAN  
Phone: (909)985-7211

Searching...  
Done.

| Source | Rx Number | Brand Name | Fill Date | Refill Y/N | Prescribing Physician | Quantity | Co-Pay |
|---|---|---|---|---|---|---|---|
| MedImpact | 0000962128 | GLUCOPHAGE | 06/03/98 | 01 | | 0 | 12.0 |
| Dose Per Day 3.0 | | | | | | | |
| MedImpact | 0000958304 | GLIPIZIDE | 06/03/98 | 01 | MICHAEL CORTEZ | 0 | 7.0 |
| Dose Per Day 4.0 | | | | | JAMES R STEWART | | |
| MedImpact | 0000962138 | GLUCOPHAGE | 07/13/98 | 01 | MICHAEL CORTEZ | 0 | 12.0 |
| Dose Per Day 3.0 | | | | | | | |
| MedImpact | 0000958304 | GLIPIZIDE | 07/13/98 | 01 | JAMES R STEWART | 0 | 7.0 |
| Dose Per Day 4.0 | | | | | | | |

Sidebar:
- Summary
- Claims
- Encounters
- Medications
- Authorizations
- Test Results
- Clinical Alerts
- Main Menu

04 August 1998

FLORENCE MELIN
4116 LAUREL GROVE
ALTADENA  CA  910013915

Dear _____ (Enter Member Name)

We wanted you and your caregiver to know that there are many community services that may be of assistance to you. Transportation, emergency response systems, and caregiver support groups, are a few of these community services that may help meet your needs.

Enclosed is a brochure on caregiving that outlines resources available from the American Association of Retired Persons. CareAmerica also provides a respite benefit that supports patients and their caregivers. This benefit provides short term assistance within the home. Please call me at (800) 445-2521 for information on the eligibility requirements for CareAmerica's respite benefit or if you like information about other community resources.

Sincerely,

CC 2
Coordination Specialist

Send Letter

Print
Envelop LJ4
SOP 1A1
SOP 1B1
SOP 8E2
SOP 10A1
SOP 12A1
SOP 17A1
SOP 17B1
SOP 18A1
SOP 18A5
SOP 19B1
SOP 26A2
SOP 29A1
SOP 29A3
Education
Coordination Plan
Main Menu Generate Letter — 180

Transfer Member

Member: 10000010266 - FLORENCE ELISE MELIN
Phone: (626) 777-7777

PCP: LUKE CHAN
Phone: (909) 985-7211

Last Name: [        ]  [Search]

Member                              Coordinator
[MELIN, FLORENCE ELISE - 10000010266 ▽]  to  [CC 1 ▽]

Transfer Reason [Community Resource(s) ▽]

[Submit]

*Main Menu*

*Member Look Up*
*Transfer Member*
*Demographics*
*Eligibility*
*Notifications*
*Coordination Plan*
*Summary*
*Assessments*
*Resources*
*Provider Referral*
*Help*
*Change Password*

Problems and Goals — 194

Member: 900000000006 — THOMAS J LIMONES
Member Address: 808 MICHAEL DRIVE
ENCINO, CA 913333345
Phone: (818) 999-9555

PCP: SIDNEY G WHITE
Phone: (818) 340-8080

Problems | Date Initiated
- #1 Home health sevices not ordered
- #2 Lab tests not routinely done to monitor med(s) — 09/18/1998
- #3 Ordered home health services not provided — 09/18/1998
- #4 Home health services not ordered — 09/18/1998
- #5 Lab tests not routinely done to monitor med(s) — 10/08/1998
- #6 Ordered home health services not provided — 10/08/1998
- #7 Home health services not ordered — 10/08/1998
- #8 Ordered home health services not provided — 10/15/1998
- #9 Lacks an appropriate plan for coverage — 10/15/1998
- #10 Lacks an appropriate plan for coverage — 11/04/1998
-                                                 — 11/06/1998

Goals | Target Goal | Target Date | Goal Attainment | Date Met | Status
- Demonstrates knowledge-coverage plan | 0% | | 0% | | News | UPDATE
  Associated Problems: #9  #10
- Develops a plan for coverage | 0% | | 0% | | News | UPDATE
  Associated Problems: #9  #10
- Identifies options for coverage | 0% | | 0% | | News | UPDATE
  Associated Problems: #9  #10
- Obtains timely home health services
  Associated Problems: #1  #4  #7  #3  #5  #8
- Schedule routine lab tests to monitor med(s) | 0% | | 0% | | News | UPDATE
  Associated Problems: #2  #5

Sidebar — 195:
- Coordination Plan
- Intervention Summary
- Intervention History
- Member Resources
- Member Characteristi
- Send Summ Report
- Send Letter
- Schedule Follow Up
- Resources
- Create SOP
- Assessments
- Notepad
- Problems/Go
- Problems/Go History
- Summary

Problems and Goals History — 196

| | | | | |
|---|---|---|---|---|
| Member: | 1000000124 | 46-LOIS M. ACKER | PCP: | ROY L. SAENZ |
| Member Address: | 416 JEFFRIES AVE SPC 62 | | Phone: | (626) 358-1897 |
| | MONROVIA, CA 910164961 | | | |
| Phone: | (626) 446-3881 | | | |

| Problems | Date |
|---|---|
| Caregiver needed to meet new needs | 09/21/1998 |
| Failure to inform physician of symptoms | |
| Has not received a pneumovax | |
| High alcohol use | |
| Home health sevices not ordered | |
| Lack of a DPAHC | |
| Lacks treatment for depression | |
| Ordered medical equip/supplies not delivered | |
| Physician(s) does not have copy of DPAHC | |

| Goals | Target Goal | Target Date | Goal Attainment | Completed Date | |
|---|---|---|---|---|---|
| Demonstrates knowledge-DPAHC | 40% | 09/14/1998 | 30% | 09/14/1998 | UNDO |
| Demonstrates knowledge-copy to physician | 100% | 09/15/1998 | 100% | 09/14/1998 | UNDO |
| Executes a DPAHC | 100% | 09/15/1998 | 100% | 09/14/1998 | UNDO |
| Modifies drinking behavior | 40% | 10/05/1998 | 10% | 09/14/1998 | UNDO |
| Provides physician(s) copy of DPAHC | 100% | 09/15/1998 | 100% | 09/14/1998 | UNDO |
| Receives pneumovax, when appropriate | 0% | 09/14/1998 | 0% | | |
| Communicates symptoms to physician | 0% | | 0% | | |
| Demonstrates knowledge-authorization process | 40% | 10/13/1998 | 60% | 09/12/1998 | |
| Demonstrates knowledge-authorization process | 40% | 10/01/1998 | 70% | 09/12/1998 | |
| Demonstrates knowledge-communicate symptoms | 0% | | 0% | | |

Sidebar (202): Coordination Plan, Intervention Summary, Intervention History, Member Resources, Member Characteristi, Send Summ Report, Send Letter, Schedule Follow Up, Resources, Create SOP, Assessments, Notepad, Problems/Go, Problems/Go History, Summary — 200

FIG. 40

VIHMS Summary Report

205

Member: 900000000006 - THOMAS J LIMONES          PCP:    SIDNEY G WHITE
Member Address: 808 MICHAEL DRIVE                Phone:  (818) 340-8080
                ENCINO, CA 913333345
Phone:          (818) 999-9555

Date [▽]                                         [View Old]

Address:
  808 Michael Drive                              Date of Birth:
  Encino, CA 913333345                             June 20, 1921

Summary Report Date: December 21, 1998   Contact Reason: [Emergency room visit ▽] [Select]

Coordination Plan
Intervention Summary
Intervention History
Member Resources
Member Characteristics
Send Summary Report
Send Letter
Schedule Follow Up
Resources
Create SOP
Assessments
Notepad
Problems/Goals
Problems/Goals History
Summary
Main Menu

FIG. 41

SYSTEM FOR MONITORING AND MANAGING THE HEALTH CARE OF A PATIENT POPULATION

BACKGROUND OF THE INVENTION

1. Field of the Invention

The present invention relates to software and hardware systems for proactively monitoring and managing the health care of a population of member patients. More particularly, the present invention relates to a proactive system in which medical data are periodically gathered and, based on medical data indicating a risk situation, Coordination Specialists are notified and provided with information enabling them to take specific actions to avoid unintended health care utilization and/or health care process failures.

2. Description of the Related Art

Conventional systems for providing health care services operate mainly in response to existing health problems. For example, in such reactive systems, a patient experiencing health problems must initially schedule an appointment with a physician for evaluation of the problems. During the appointment, the physician evaluates the patient, the patient is treated by the physician or is referred to a specialist physician for treatment, and the patient is prescribed medicine or other types of follow-up care/treatment.

Accordingly, the effectiveness of conventional reactive systems in their ability to maintain patient health depends heavily upon patient responsibility. For example, conventional systems require a patient to determine when to seek medical help, to determine where to go for help (physician's office, outpatient clinic, hospital, emergency room, etc.), to understand his condition and his role in treatments), to comply with prescribed treatment, and to manage multiple conditions and corresponding treatments simultaneously. In a case that any of these functions is poorly performed, the health of the patient is jeopardized and additional health care expenditures are likely to be necessary.

Conventional systems also require several physicians or other care providers to care for a particular patient. In some of these systems, for example, a primary care physician focuses on diagnosis and development of a treatment plan, a specialist physician focuses on a particular specialty area, a surgeon performs needed surgeries, and a home health care provider delivers home-based treatment and support. However, conventional systems often fail to cooperatively execute each of the above health care processes, most often due to a lack of communication among the various care providers.

As a result of the foregoing, conventional health care systems are susceptible to several types of process failures. These failures often lead to lower quality of care and higher health care costs. In one type of process failure, a patient fails to fulfill his responsibilities in managing his condition or executing his health care regimen. Specifically, a patient with hypertension may not properly manage his condition by lowering his sodium intake, or a patient with dementia and no caregiver support may be unable to properly manage multiple prescribed medications.

Another type of process failure occurs when health care is not consistently delivered to patients with progressive chronic conditions. For example, a patient with heart problems who is taking blood-thinning agents may fail to undergo required periodic lab tests due to either patient non-compliance or neglect on the part of the primary care physician. In another example, a patient with diabetes, at risk for deteriorating vision, may fail to attend annual eye examinations.

Communication failures are another type of process failure and occur between various care providers. In one instance, due to a lack of communication with a patient's primary care physician, a hospital-based physician may prescribe care for an elderly patient that is in conflict with the primary care physician's treatment plan and understanding of the patient. In another instance, a specialist may perform lab tests identical to those previously performed by a primary care physician because he is unaware of the previous tests or because he does not have access to the results of the previous tests.

Failures in task execution may occur even if communication between various providers is successful. For example, even though instructions are issued to provide a wheelchair to the home of a discharged patient, those instructions may not be carried out, or may be carried out several days too late. In either case, the health of the patient is jeopardized.

Improper utilization of health care resources is another common type of process failure. For example, a patient with a chronic condition and poor understanding of the health care system may use the emergency room for health care services when other options would be more appropriate and much less costly. In another example, improper utilization of resources also may occur when a patient ignores serious symptoms of disease and, as a result, fails to seek care. In this latter case, the health of the patient is endangered and the potential costs of future care for that patient may increase substantially.

Finally, conventional health care systems are effective only if providers follow accepted standards of care, whether in prescribing medicine, rehabilitation, or other treatment. If such standards are not followed, patient health is jeopardized even if all other aspects of the system function properly.

As a result of the prevalence of process failures in conventional health care delivery systems, health care providers, health maintenance organizations (HMOs), and medical insurance companies are attempting to create and enforce strict protocols to deal with health problems once they occur, and to perform limited preventive care for certain individuals. However, these conventional protocols have not adequately improved the health of individuals subject to the protocols, nor have they sufficiently reduced health care costs.

SUMMARY OF THE INVENTION

In order to address the foregoing problems, the present Applicants have discovered that certain combinations of patient characteristics and medical events concerning a patient indicate that the patient is at risk of incurring medical costs due to an avoidable process failure of the health care system. Such combinations are hereinafter referred to as "risk situations". Moreover, Applicants have invented a system which detects risk situations and allows care providers to proactively address avoidable process failures that correspond to the risk situations.

Advantageously, the present invention allows proactive intervention in cases where the cost of preventing a process failure is less than the cost incurred if the failure occurs, as reduced by the probability of the failure occurring without the intervention. Accordingly, the present invention provides a flexible and proactive system to improve the health of a population of member patients and to lower the costs of caring for the population. The system also provides proactive intervention in cases where the above cost-benefit relationship is not satisfied, but where intervention is nonetheless desired, such as to meet a regulatory requirement.

More specifically, a system for managing health care of a member population according to the present invention preferably includes periodic monitoring of a member population for member characteristics and/or medical events, identification of opportunities to assist members in managing their health and in navigating through the health care system based on combinations of member characteristics and/or medical events, and identification, based on combinations of member characteristics and medical events, of opportunities to assist physicians and other care providers in properly delivering health care services.

A system according to the invention also preferably includes proactive, cost-effective, and coordinated patient interventions to address the identified opportunities, as well as-proactive interventions with physicians and providers to assist them in managing care and in coordinating the activities of various care providers.

FIG. 1 is a representative block diagram of a system according to the present invention. As shown, member characteristics 10 are obtained from member surveys 11, health care providers 12, historical health care data 13, such as laboratory data, pharmacy data, or claims data, while data concerning medical events 14 are periodically obtained from data sources such as laboratories 15, pharmacy benefits managers 16, insurance companies 17, health plans 18, or hospitals 19. Based on a detected combination of member characteristics 10 and/or medical events 14 indicating a risk situation, notification 20 is generated.

Notification 20 is sent to Coordination Specialist 21 and may also include information used to update member characteristics 10. Coordination Specialist 21 is preferably a medically-trained individual who is responsible for monitoring and managing a particular subset of the member population. As a result, it is beneficial for Coordination Specialist 21 to receive any notifications regarding members of the subset. As will be described, the system also provides Coordination Specialist 21 with access to a wide range of medical data concerning members of the subset, as well as instructions and tools to manage the health care of the members.

Also sent with notification 20 is information concerning an intervention which should be performed by Coordination Specialist 21. The intervention is designed to address an avoidable process failure corresponding to the indicated risk situation indicated by notification 20. In order to execute the intervention, Coordination Specialist 21 may be required to contact physician 22, disease-specific case manager 23, member 24, hospital 25, durable medical equipment provider 26, health plan 29, or another health care-related entity, or to refer to education resources 27 or arrange community resources 28. It should be noted that notification 20 and/or its associated intervention(s) may be sent directly to any of the above health care-related entities or other entities utilizing the present invention.

Accordingly, in one aspect, the present invention is a system for managing health care of a plurality of members in which member characteristics of a member are identified, a list of the member characteristics are stored, information indicative of a medical event is continuously monitored, information indicative of a medical event is obtained, and a risk situation is automatically identified based on the member characteristics and the medical event information. A notification is generated in response to the identified risk situation, wherein the notification is accompanied by a predetermined script, or Standard Operating Procedure (SOP), designed to address the identified risk situation.

Preferably, the risk situation corresponds to a potential process failure in the delivery of health care to the member.

In even greater detail, the present invention is a system for managing health care processes in which member characteristics of each member of a patient population are determined from member surveys, care providers, insurance claim data, historical health care data or the like, and medical events are periodically detected from laboratory data, pharmacy benefits manager data, hospital data, physician records, home health care data, direct conversations with members and physicians, health plan data or other sources.

The detected medical events and member data are received at a centralized location, where they are linked to individual members using a master person index, and stored in a database based on the linkages. Next, member data and medical events corresponding to a member are assessed to determine whether there exist risk situations which indicate a potential process failure in the health care system.

For example, the following combinations of member characteristics and/or medical events represent risk situations: diabetes, hypertension and high sodium levels, dementia and no caregiver support, heart problems and no prescribed beta blockers, discharge of an elderly patient who lacks caregiver support, and presence of a chronic condition, a hospitalization medical event, and no caregiver support.

Upon identifying a risk situation, a notification is sent to a Coordination Specialist and/or to another selected entity. The notification specifies the risk situation and includes a coordination plan that provides relevant information to the Coordination Specialist and guides appropriate intervention processes. Such a notification may be delivered via Internet, Intranet, or other means. Received notifications are preferably prioritized based on their urgency.

In order to respond to a notification, the Coordination Specialist performs steps of a particular SOP corresponding to the coordination plan. The SOP details specific steps to address the risk situation represented by the notification, and may include direction of the member to community resources, education of the member, or a further assessment of the member's characteristics, the results of which can then be used to update the member's characteristics. The SOP may also result in automatic facsimile transmission of medical and coordination information to a provider, generation of reminder letters, or provider paging.

A preferred embodiment of the invention also includes software applications which allow care providers to enter referrals, provide additional information, check recent activities, order tests, or the like. Such events are detected by the system and are assessed to update member characteristics and/or to generate notifications.

As an example of the foregoing, a case is considered in which a particular member's characteristics include lack of a caregiver. In one embodiment of the invention, hospitalization and lack of a caregiver are a combination indicating a risk situation. Accordingly, in a case that the member is hospitalized for knee replacement surgery, a "hospitalization" medical event is detected. Next, the system identifies the presence of the hospitalization/lack of a caregiver risk situation and generates a corresponding notification.

A Coordination Specialist receives the notification and is directed to perform an SOP based on the notification. The SOP may include steps such as confirming a discharge plan, education for the member, and the securing of durable medical equipment for the member, such as a wheelchair.

More specifically, FIG. 2 is a flow diagram of process steps executed by a Coordination Specialist according to the present invention. Initially, in step S201, the Coordination Specialist logs on to the system via a computer terminal. Next, in step S202, the Coordination Specialist reviews a displayed list of notifications received by the system since a previous logon. Preferably, the list also includes notifications not yet acted upon by the Coordination Specialist. The notifications may be sorted according to urgency, notification type, or in an alphabetized list of affected members.

In step S204, the Coordination Specialist selects a member corresponding to one of the displayed notifications. This selection causes the system to present data regarding the notification to the Coordination Specialist. Eligibility information for the member is then checked in step S205 to determine the insurance eligibility status of the member. Next, in order to obtain an overview of relevant information, the Coordination Specialist reviews member characteristics of the selected member in step S206. As described above, the characteristics may include such characteristics as terminal illness, substance abuse, reliance on a caregiver, failure to seek care, or the like.

In step S207, the Coordination Specialist examines whether an intervention history for the member is available. If so, flow proceeds to step S209, wherein the intervention history is displayed and reviewed by the Coordination Specialist to obtain a clearer understanding of the member's current health situation. Flow continues from either step S207 or S209 to step S210, at which point the Coordination Specialist reviews other data related to the member, such as medication data, encounter data, or assessment data. The Coordination Specialist also views, in step S211, the actual questions and answers of a member health survey previously received from the member.

In step S212, the Coordination Specialist reviews and implements interventions based on SOPs of a notification corresponding to the member selected in step S202. As described above, an intervention may consist of contacting the member, the member's primary physician, a related provider, community resources, a pharmacy benefits manager, or the like. After performing the intervention, in step S214, the Coordination Specialist completes a coordination plan and notes the time required to complete the intervention in an intervention summary for the completed intervention, the information of which is thereafter recorded within an intervention history for the member.

In step S215, the Coordination Specialist updates the member characteristics for the member. Alternatively, based on information obtained during the intervention, the system may automatically update the member characteristics. Lastly, the Coordination Specialist removes the processed notification in step S216 and selects a next member in step S217.

The foregoing process steps advantageously provide fast, informed, and proactive management of member's health situations. As a result, the present invention can improve member health while reducing health care costs.

This brief summary has been provided so that the nature of the invention may be understood quickly. A more complete understanding of the invention can be obtained by reference to the following detailed description of the preferred embodiments thereof in connection with the attached drawings.

BRIEF DESCRIPTION OF THE DRAWINGS

FIG. 18 is a view of a Notification Details page and a Main Menu frame for use in conjunction with the present invention.

FIG. 19 is a view of an Eligibility page and a Main Menu frame for use in conjunction with the present invention.

FIG. 20 is a view of a Demographics page and a Main Menu frame for use in conjunction with the present invention.

FIG. 21 is a view of an Edit Demographics page and a Main Menu frame for use in conjunction with the present invention.

FIG. 22 is a view of an Member Profile page and a Main Menu frame for use in conjunction with the present invention.

FIG. 25 is a view of a World Wide Web browser display and a java applet window in accordance with the present invention.

FIG. 27 is a view of an Intervention History page and a Coordination Plan frame for use in conjunction with the present invention.

FIG. 30 is a view of a Claims page and a Summary frame for use in conjunction with the present invention.

FIG. 31 is a view of a Medications page and a Summary frame for use in conjunction with the present invention.

FIG. 32 is a view of an Intervention Summary page and a Coordination Plan frame for use in conjunction with the present invention.

FIG. 34 is a view of a Community Resources page and a Resources frame for use in conjunction with the present invention.

FIG. 35 is a view of an HTML page and a Send Letter frame for use in conjunction with the present invention.

FIG. 36 is a view of a Create SOP page and a Coordination Plan frame for use in conjunction with the present invention.

FIG. 37 is a view of a Schedule Follow Up page and a Coordination Plan frame for use in conjunction with the present invention.

FIG. 38 is a view of a Transfer Member page and a Main Menu frame for use in conjunction with the present invention.

FIG. 39 is a view of a Problems and Goals page and a Coordination Plan frame for use in conjunction with the present invention.

FIG. 40 is a view of a Problems and Goals History page and a Coordination Plan frame for use in conjunction with the present invention.

FIG. 41 is a view of an VIHMS Summary Report page and a Coordination Plan frame for use in conjunction with the present invention.

DETAILED DESCRIPTION OF THE PREFERRED EMBODIMENTS

I. Hardware and Software Architecture

Figure 1:
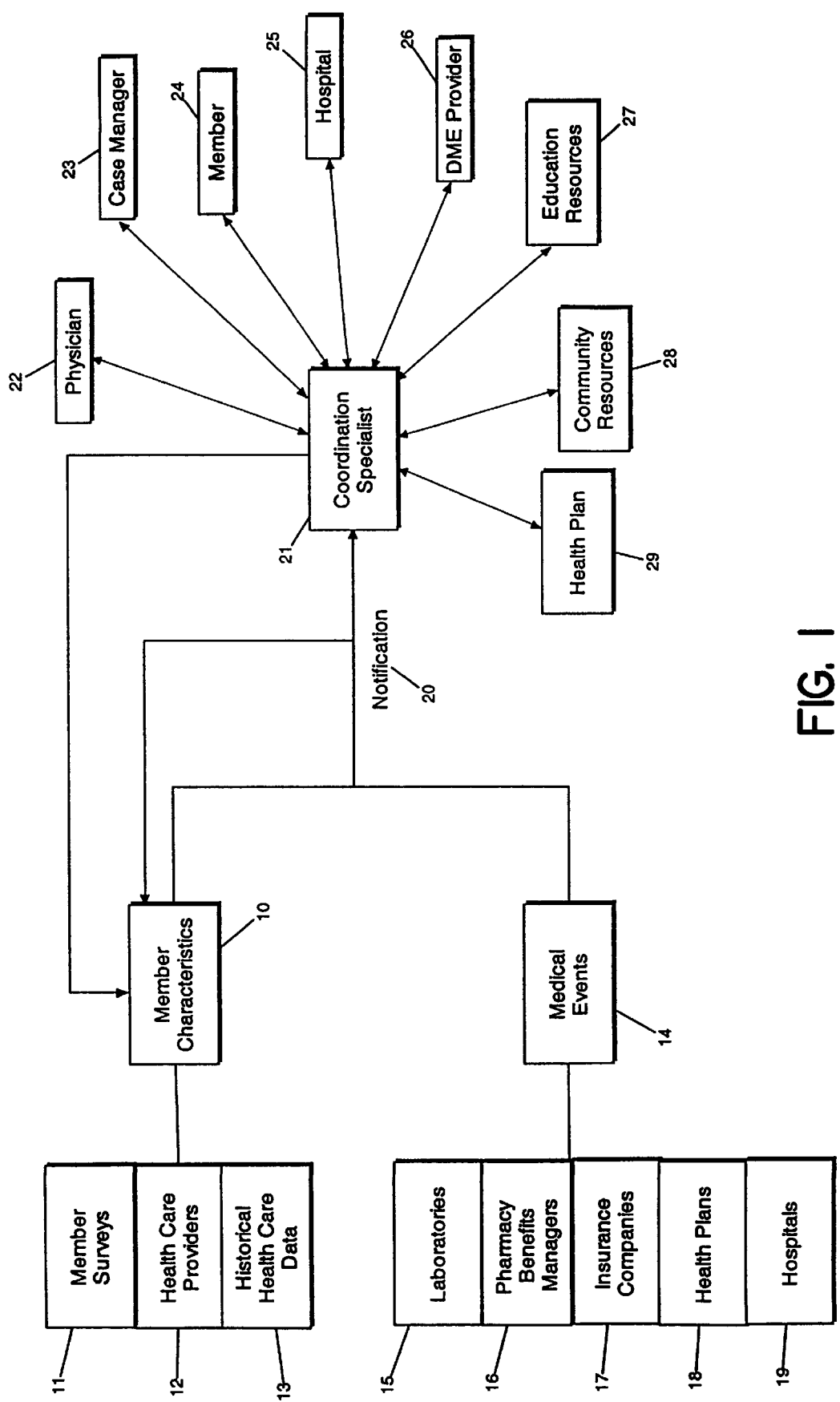
FIG. 1 is a functional block diagram illustrating data and process flow according to one embodiment of the present invention.
Figure 2:
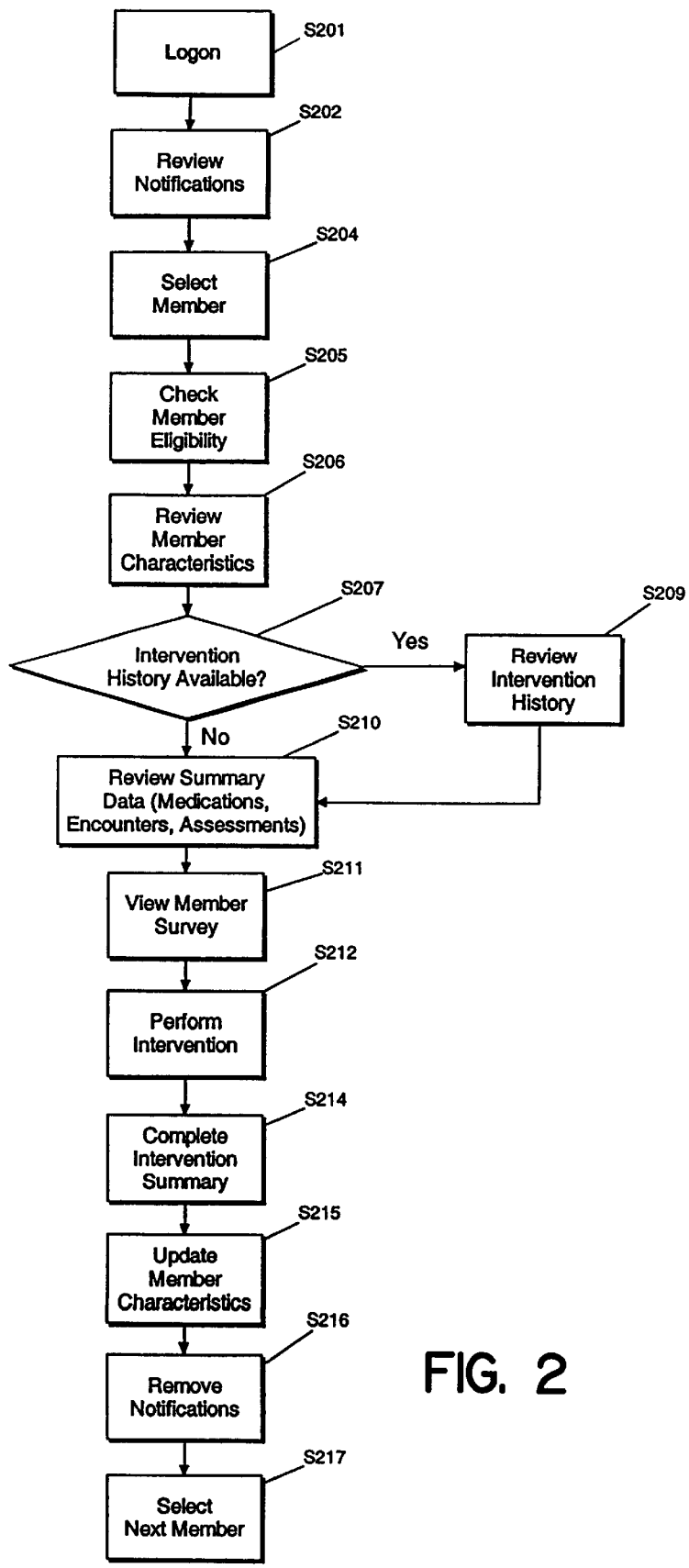
FIG. 2 is a flow diagram of process steps executed by a Coordination Specialist according to the invention.
Figure 3:
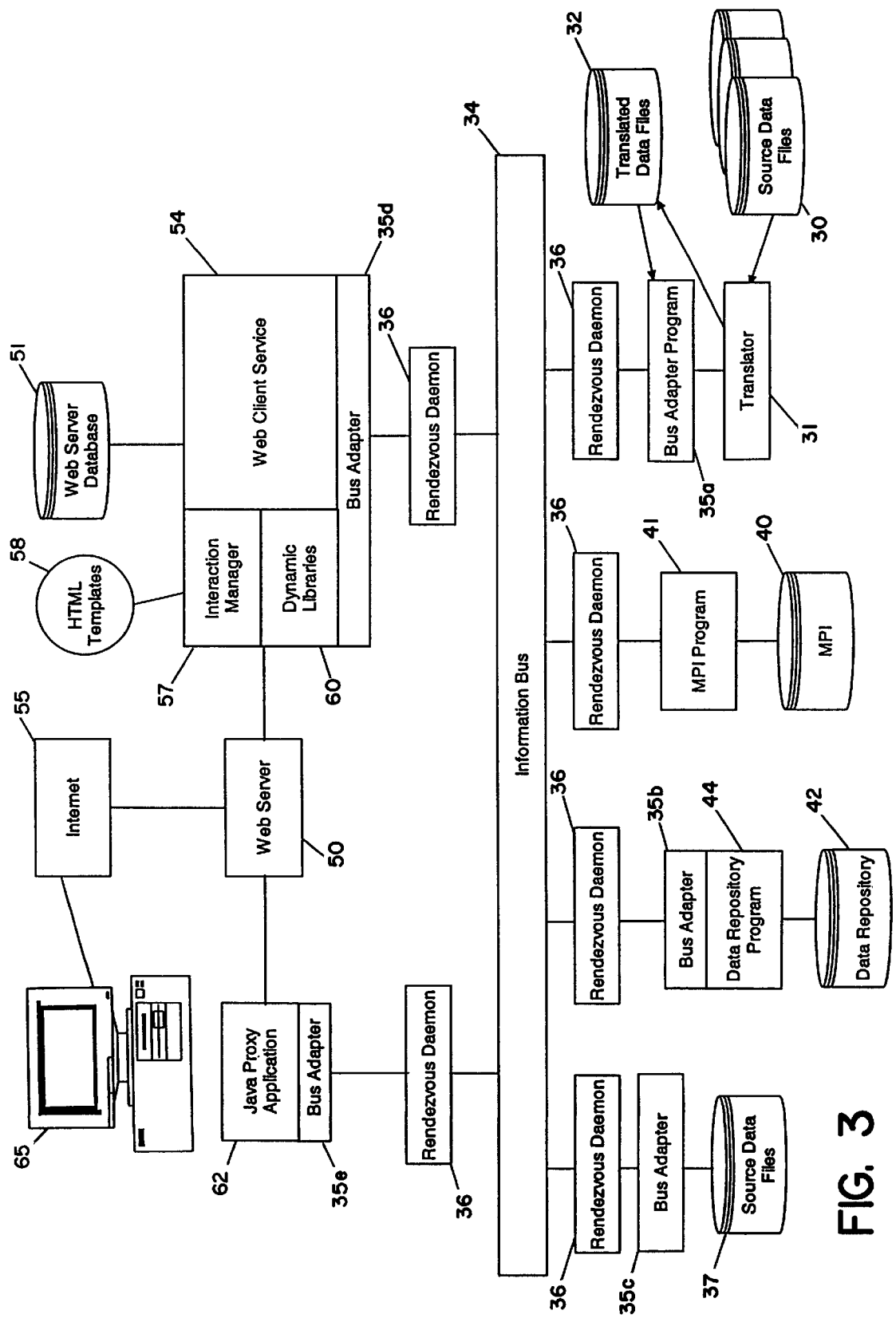
FIG. 3 is a block diagram of a hardware and software architecture according to the present invention.

FIG. 3 is a block diagram illustrating a hardware and software architecture according to the preferred embodiment of the present invention.

A. Source Data Files

Source data files 30 are obtained from various legacy data systems currently in place within health care-related entities. In this regard, source data files 30 may be provided by a hospital, an outpatient lab, a home health agency, a durable medical equipment vendor, a hospital discharge planner, a physician, an answering service, an outpatient medical record, a treatment facility, a medical insurance claim company, a primary care physician, a pharmacy benefits manager, a health plan, or any other source of health-related data.

Data contained in source data files 30 are in a variety of legacy data formats. Moreover, each source data file contains a legacy key identifying a person to whom the data file pertains. Accordingly, a person may be identified by a particular legacy key in one legacy data system and by another legacy key in another legacy data system.

B. Translator

Source data files 30 may be transferred to translator 31 via the Internet, an Intranet, a portable computer storage device, such as a floppy disk or magnetic tape, or any other suitable system. In this regard, since source data files 30 originate from heterogenous legacy data systems, translator 31 translates source data files 30 into a common format for use in the present invention.

In a preferred embodiment, translator 31 consists of two elements. The first element is a translation program, such as Mercator®, which receives a data file having a first format and translates the data file into an output file having a second format. The second element consists of maps used by the translation program to translate data files from the first format to the second format. The output data files are stored as translated data files 32.

The primary function of translator 31 is to provide mapping of source data files to standard data elements and code value names. To do so, translator 31 performs data element mapping and data code translation. Regarding data element mapping, certain data elements from source data files are identified as useful to the present system. Accordingly, these data elements are assigned a standard data element name for use within the system. In a case that translator 31 detects a useful data element from source data files 30, the data element is mapped to the standard data element name, regardless of how the element is represented within source data files 30. For example, various legacy data systems may represent member gender using data elements "Gender" or "Sex". In this regard, the data element mapping feature of translator 31 will translate each of the source system data elements to a standard data element name, such as "MemberSex".

For each data element used by the system, translator 31 will also translate data codes for the data element to a common format. For example, legacy system code values represented by numeric codes, such as "1"=Male and "2"= Female, can be translated to common alpha code values, such as "M" and "F".

Although any type of data translation program can be used in practicing the invention, a translation program utilizing map-driven translation advantageously provides good adaptability for handling various source file formats.

C. Information Bus

Translated data files 32 move throughout the FIG. 3 system by means of information bus 34. Information bus 34 is preferably a publish-and-subscribe message bus such as that provided by TIBCO™. Such a messaging system allows event information and other data to be shared among diverse applications, and also eliminates any need for point-to-point addressing. Generally, messages published on information bus 34 are attached to a header which can indicate the source, content, or intended destination of the message. Accordingly, various applications on information bus 34 subscribe to messages based on message source, data type, or intended destination, and thereby retrieve messages from information bus 34. Advantageously, by integrating various applications through such messaging, the system is flexible and tolerant of changes in information flow. Of course, use of publish-and-subscribe messaging is most beneficial in a case where messages share a common format which can be understood by any process accessing information bus 34, such as the common format provided by translator 31.

It should, however, be understood that the present invention is not limited to use of a publish-and-subscribe messaging system. Rather, the present invention can be used in conjunction with any system for passing data among various applications.

Bus adapter 35a is provided to integrate translator 31 and translated data files 32 with information bus 34. Bus adapter 35a packages translated data files 32 into a format which can be published on information bus 34. To do so, bus adapter 35a parses a file of translated data files 32, extracts the field names and values, and accumulates the extracted information along with a header into a composite message.

Bus adapter 35a also calls application programming interface (API) functions of rendezvous daemon 36, provided by TIBCO™. Rendezvous daemon 36 is a communication process that ensures reliable message transmission by guaranteeing packet delivery, by packetizing and reassembling messages, by filtering subject addressed messages, by dispatching messages to application processes, and by shielding programmers from operating system idiosyncracies. Rendezvous daemon 36 runs on each system connected to information bus 34. If rendezvous daemon 36 is not running, it will be automatically triggered once its API functions are called. Bus adapter 35a and rendezvous daemon 36 may also work together to subscribe to messages on information bus 34, and to pass these messages through translator 31 for storage in source data files 30 in an appropriate legacy data format.

It should be recognized that source data files 37 of FIG. 3 are in a common system format, and therefore need not be translated for publication on information bus 34. Accordingly, such files are simply published using bus adapter 35c and using rendezvous daemon 36 as described above.

D. Master Person Index

The system also preferably includes master person index (MPI) 40, such as that available from Madison Technologies™. Master person index 40 is connected to information bus 34 through rendezvous daemon 36 and through MPI program 41. Particularly, MPI program 41 includes a bus adapter which formats data from MPI 40 into a message format for publication on information bus 34. Accordingly, MPI program 41 utilizes API function calls to rendezvous daemon 36 for such publication, as well as for subscription to messages published on information bus 34.

For purposes of clarification, each of the bus adapter-rendezvous daemon combinations described herein performs the general functions described above. However, since the various bus adapters are customized according to their input data, each bus adapter is designated uniquely by one of numerals 35a to 35e.

Figure 4:
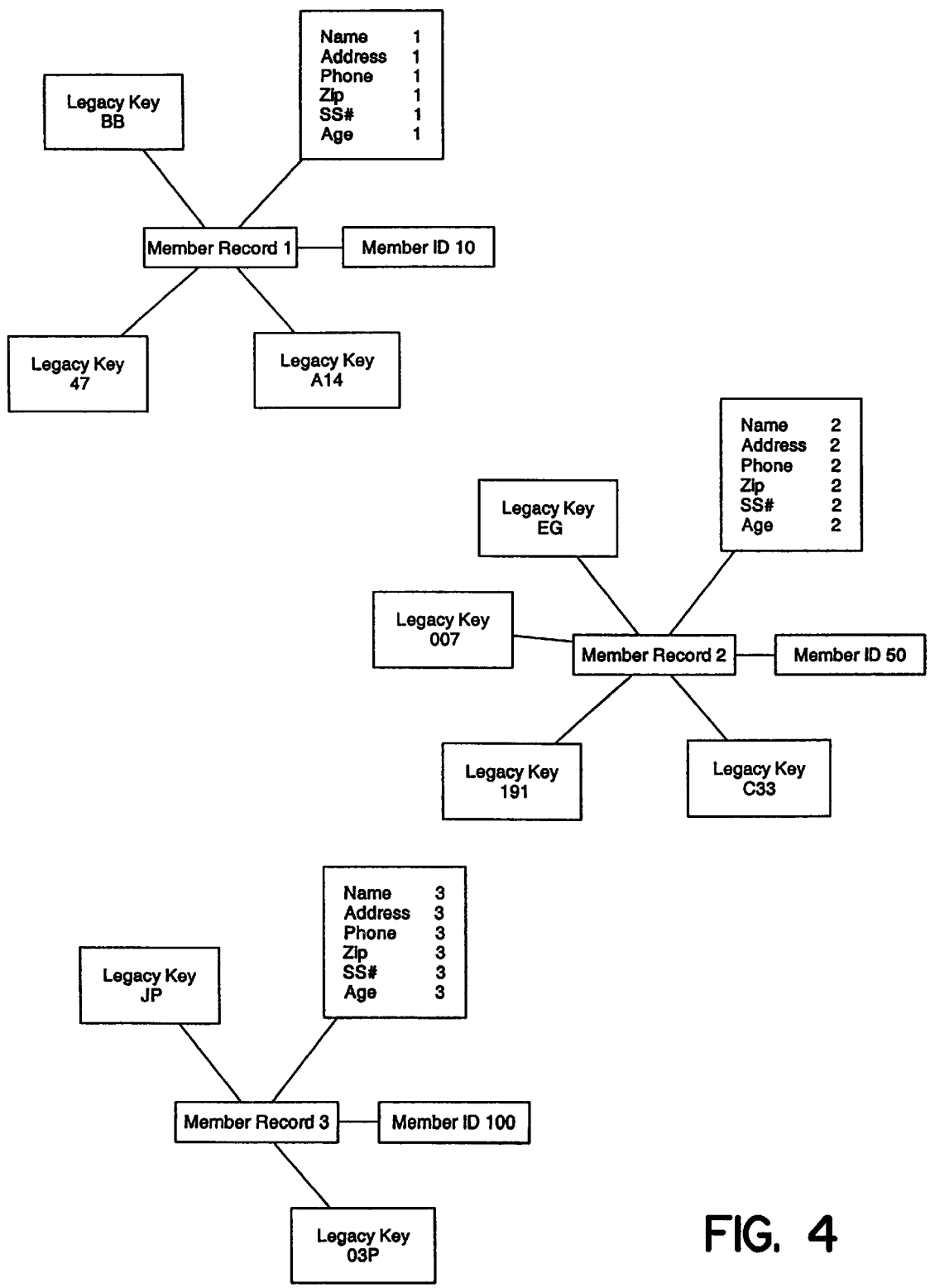
FIG. 4 is a block representation of data stored in a Master Person Index according to the present invention.

FIG. 4 illustrates data relationships within MPI 40. As shown, a member is primarily represented within MPI 40 by a member record number. Associated with each record number are demographics data for the member, such as name, address, phone number, zip code, social security number, age, etc. Each member record number is also linked to a member ID and to legacy keys which are used by various source legacy data systems to identify the member.

E. Data Repository

Data repository 42 stores translated data files published over information bus 34. In this regard, data repository program 44 subscribes to messages published by translator 31, receives a message, creates an instance of an object-oriented class capable of processing the message, and delivers the message to the class. The class parses data from the message, inserts the data into data repository 42, and publishes a "Member Data Changed" message.

Figure 5:
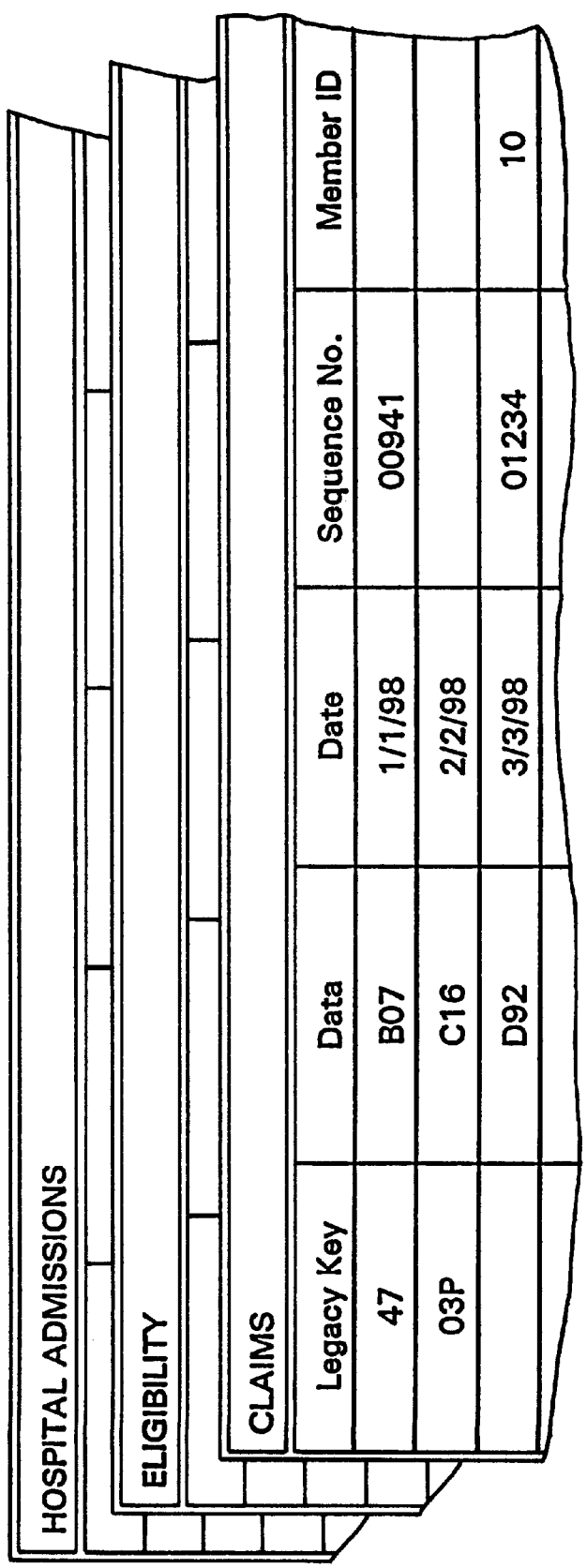
FIG. 5 is a representation of data stored in a data repository according to the present invention.

As shown in FIG. 5, data files are stored in data repository 42 within tables according to data type and are indexed according to legacy keys and/or member ID number. Data records stored in data repository 42 may also be associated with a sequence number, which will be discussed below. Data repository 42 also stores eligibility records for each member corresponding to each health plan being administered by the system. By virtue of the data storage format of data repository 42, all stored data pertaining to a particular member can be obtained from data repository 42 by referencing a member ID in conjunction with the associations stored in MPI 40. This procedure will be explained in detail in conjunction with FIG. 12 and FIG. 13.

Notably, insertion or update of certain data into data repository 42 causes firing of database triggers and execution of rules particular to the data. The rules are stored in data repository program 44 in a table format to provide flexibility to system designers, but may also be hard-coded into program 44.

Figure 6:
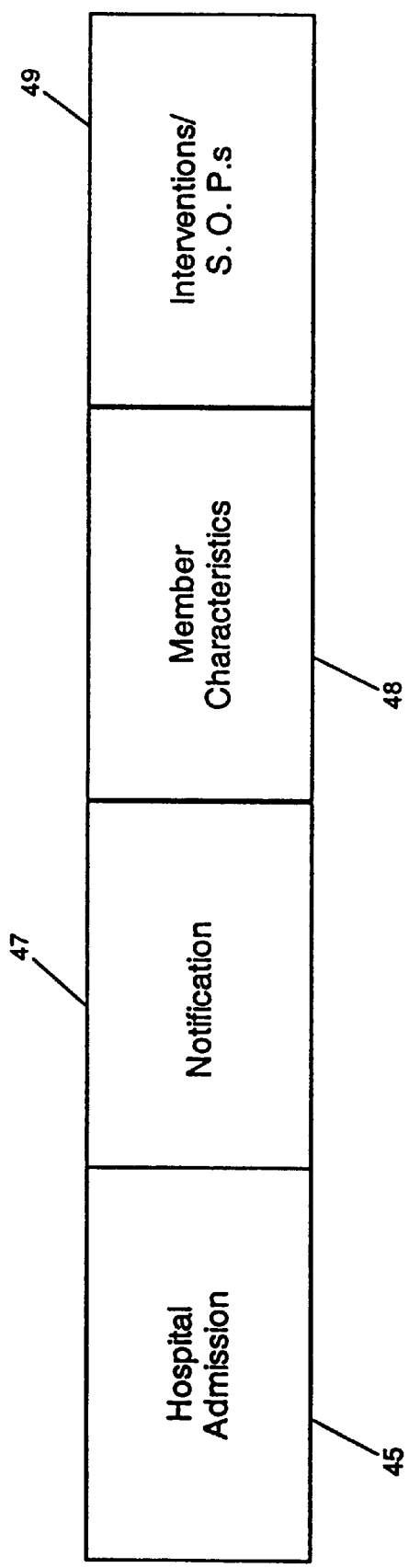
FIG. 6 is a block representation of an event-triggered rule for use in conjunction with the present invention.

FIG. 6 shows a block representation of a trigger event rule table used by data repository program 44. According to the FIG. 6 rule, storage of hospital admission data causes publication of a message, including notification 47 and interventions 49, through bus adapter 35b and rendezvous daemon 36. In addition, according to the FIG. 6 rule, member characteristics 48 of the subject member are updated.

As described above, interventions 49 may set forth several SOPs for addressing a risk situation corresponding to the hospital admission data. The SOPs may consist of contacting a provider or other health-related entity, generating a letter to a provider or member, or contacting a member to provide education or to perform a health assessment. Assessments are standardized or proprietary questionnaires in which responses are scored to provide an evaluation of a person's health situation with respect to a specific health-related issue, such as medication misunderstanding, gastrointestinal disorders, or the like.

Notification 47 may also include information indicating that the notification and associated intervention should not be directed to a Coordination Specialist, but rather to a Case Manager, who is a care provider enlisted to deal with a specific problem of a member, such as diabetes or the like.

Notifications and assessments will be described in more detail in Section III of the present application.

Data repository program 44 also subscribes to "Get Data" messages so as to receive requests for data from data repository 42 and to provide data thereto. Similarly, data repository program 44 subscribes to "Set Data" messages which are used to insert or update data in data repository 42. As described above, such insertion or updating may cause a database trigger to fire and thereby cause execution of a rule stored in data repository program 44.

Data repository program 44 preferably generates special notifications, called clinical alerts, by examining member characteristics, historical member-related data, and medical event data. Generally, clinical alerts are notifications generated based on an analysis of data from various data sources stored within the system. For example, a patient who is over 75 years old, has a history of episodic atrial fibrillation, is allergic to aspirin, and is not receiving Ticlopidine or Clopidigril is at risk for acute myocardial infarction. Therefore, a clinical alert may be designed to detect whether any patients possess these characteristics and, if so, to issue a clinical alert notification and intervention information for addressing the risk situation.

It should be noted that a clinical alert notification can also be generated based on a member characteristic and a detected lack of time-sensitive medical event data. For example, if repository program 44 identifies a member taking Coumadin who has not had a laboratory test in the last thirty days, a clinical alert notification can be generated, which may trigger an automatic reminder letter to the member or to associated provider.

Clinical alerts can be performed by a rule-based data analysis program located elsewhere in the system. However, due to the topography of the system, it is particularly advantageous for such a program to be part of data repository program 44 so as to have direct access to data repository 42.

On a similar note, member characteristics and member-related data can be analyzed by data repository program 44, or another program stored elsewhere in the system, to identify groups of at-risk members and to automatically generate notifications for alerting a Case Manager or System Administrator. Program 44 may also automatically refer or transfer such identified at-risk members to a Case Manager or automatically cause generation of education/reminder letters to the members or associated providers.

As described above, the foregoing combinations of medical events and/or member characteristics which cause generation of a notification indicate a risk situation corresponding to a potential process failure in the delivery of health care to a member.

F. Web Server

Web server 50 is also connected to information bus 35, and includes web server database 51.

1. Web Server Database

Web server database 51 contains tables of member characteristics corresponding to each member in the system. The member characteristics are obtained using standard and proprietary algorithms applied to member risk survey responses and historical health care data, and directly from health care providers. Of course, member characteristics may be gleaned from other sources as well.

Database 51 also includes data specific to coordination activities, such as scripts of SOPs corresponding to required interventions, intervention histories, intervention resources, notes concerning particular members, and other data used by the Coordination Specialist that are not needed elsewhere in the system. In this regard, it is advantageous to have the above-listed data located on web server database 51 so that the data can be quickly accessed by a Coordination Specialist. However, it should be noted that the data could be located elsewhere in the system.

2. Web Server Data Update Application

Web server 50 preferably executes a web server data update application which subscribes to messages published from data repository 42. In this regard, Member Data Changed messages, which may include notifications, interventions, and/or sequence numbers, are published by data repository 42 and received by the web server data update application over information bus 34. When such a message is received, the web server data update application parses the message, queries web server database 51 to determine whether the subject member is included in database 51, and, if so, updates a list of notifications stored in web server 51 to include any notifications passed along with the received message, and updates member characteristics stored in web server 51 based on any member characteristic data passed with the message.

3. Web Client Service

Also executing on web server 50 is web client service 54 for controlling user interaction with the system via Internet 55. In this regard, interaction manager 57 of service 54 receives a request from a user over Internet 55. Based on the request, interaction manager 57 creates an HTML page using a template from HTML templates 58 and appropriate dynamic library classes from dynamic libraries 60. The library classes are used to extract any data from database 51 which are needed to complete an HTML template. The created page can then be sent over the Internet to a web browser for viewing. Database 51 also includes java applets which can be extracted from database 51 using the dynamic library classes and thereafter sent to a web browser. Accordingly, dynamic libraries 60 include classes to retrieve the stored Member Data Changed messages, notifications, intervention histories, member characteristics, java applets, or other information.

4. Java Proxy Application

Java proxy application 62 is created on web server 50 once a Coordination Specialist logs onto the system via web client service 34. Java proxy application 62 gathers requests from executing java applets for data and, in turn, requests the required data from data repository 42. Moreover, java proxy application 62 caches the requested data as the Coordination Specialist moves between web pages so that the data do not have to be re-retrieved when rebuilding already-displayed web pages for re-transmission.

More particularly, when proxy application 62 receives a request for data from an applet via Internet 55, proxy application 62 will examine its cache to determine whether it contains the data. If so, application 62 will return the data to the applet. If the data are not in the cache, application 62 will create a Get Data request using bus adapter 35e and publish the request using rendezvous daemon 36. Accordingly, the data are received from data repository 42, and are then sent to the applet.

"Update Request" messages, which request updates to web server database 51, can be sent by applets executing on computing equipment 65 or by java proxy application 62. The web server data update application also subscribes to these messages and updates web server database 51 in accordance with the messages.

G. User Computing Equipment

Figure 7:
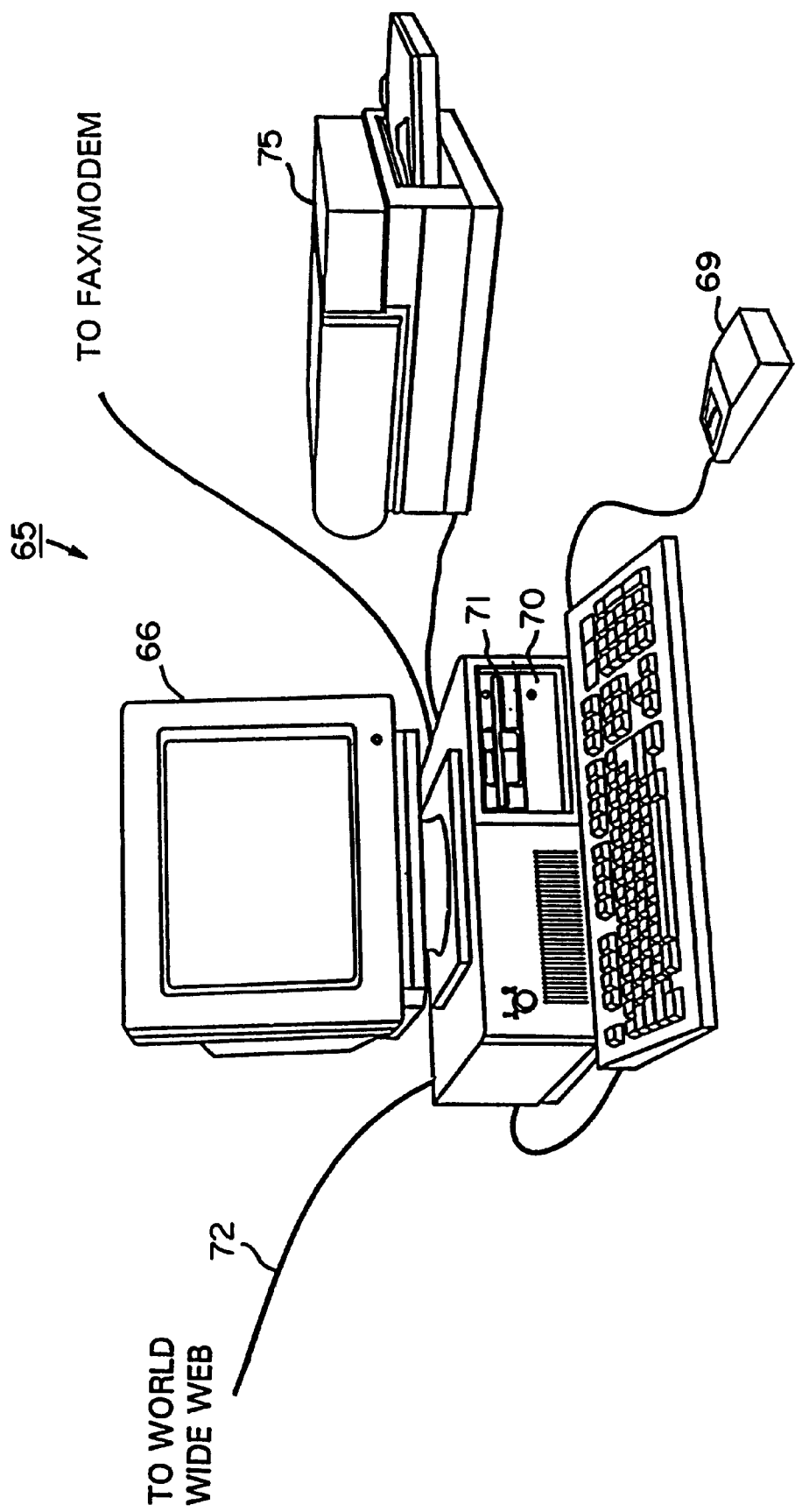
FIG. 7 is a representative view of computing equipment for use in conjunction with the present invention.

Computing equipment 65 is used by a Coordination Specialist, or other user, in order to access the information provided by the invention. FIG. 7 is an outward view of a computing system for use by a Coordination Specialist in practicing the present invention. Computing equipment 65 is preferably an IBM-PC compatible computer having a windowing environment, such as Microsoft® Windows 98®. Provided with computing equipment 65 are display screen 66, comprising a color monitor or the like, keyboard 67 for entering text data and user commands, and mouse 69 for selecting and manipulating objects displayed on display screen 66.

Computing equipment 65 also includes a computer-readable memory medium such as fixed disk 70 for providing computer-readable storage. Fixed disk 70 stores, among other files, a Java-enabled World Wide Web browser for viewing HTML pages or executing java applets received over a connection to the World Wide Web. Floppy disk drive 71 provides a means whereby computing equipment 65 can access a computer-readable floppy disk storing data files or can store data files thereto.

Also provided with computing equipment 65 is World Wide Web connection 72, which may be a network connection to a network server having access to the World Wide Web, a T1 line or an integrated services digital network (ISDN) connection directly accessing the World Wide Web, or a modem connection. Using World Wide Web connection 72, computing equipment 65 can receive HTML pages, download and execute Java applets, and download data files located on the World Wide Web.

Fax/modem connection 74 can be used to directly transmit facsimile messages over telephone lines or to connect to a remote computer via a modem. Also included is printer 75 for obtaining hard copy output of images displayed on display screen 66 or other files downloaded to computing equipment 65.

Figure 8:
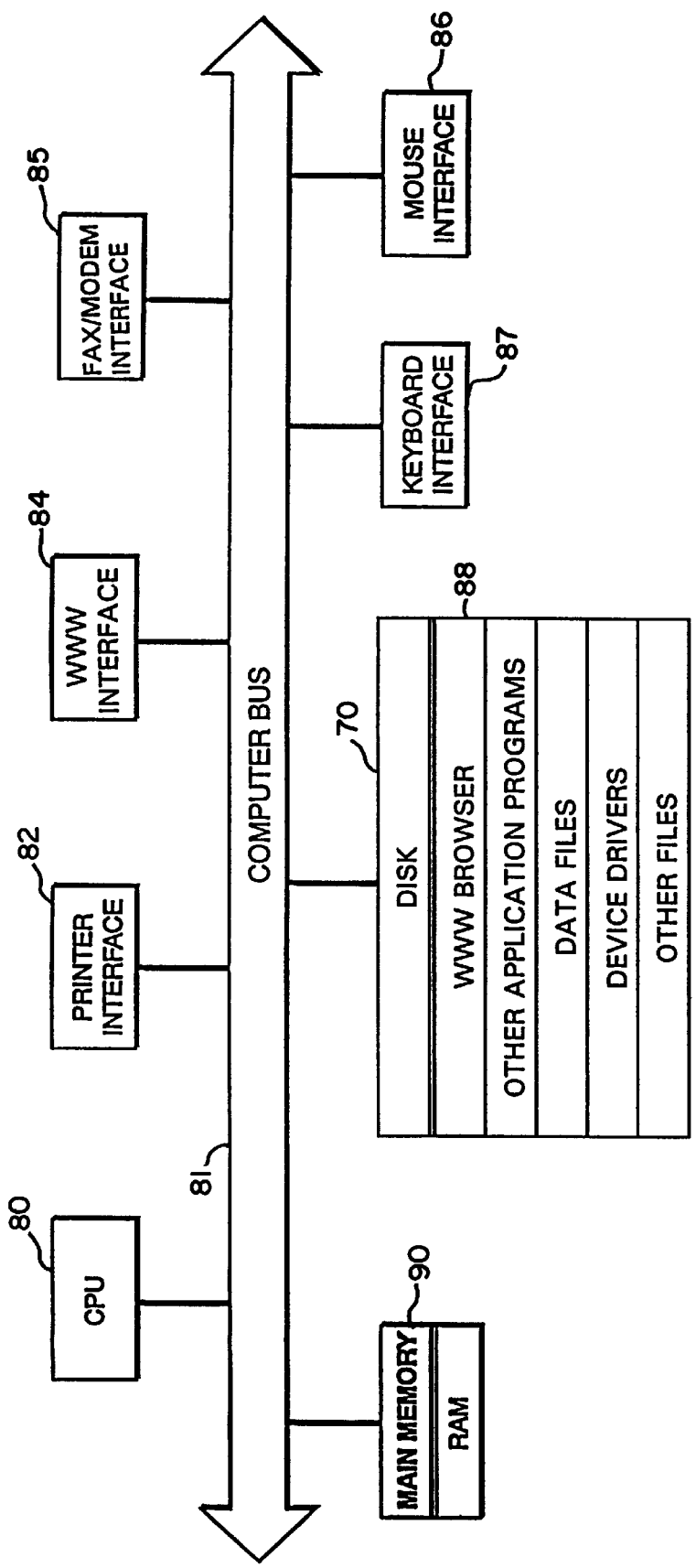
FIG. 8 is a block diagram illustrating the internal architecture of the FIG. 7 computing equipment.

FIG. 8 is a block diagram showing the internal functional architecture of computing equipment 65. As shown in FIG. 8, computing equipment 65 includes CPU 80 for executing computer-executable process steps. CPU 80 interfaces with computer bus 81 along with printer interface 82, World Wide Web interface 84, fax modem interface 85, mouse interface 86, and keyboard interface 87.

Disk 70 includes a section for storing computer-executable process steps of World Wide Web browser application 88 and of other application programs. Disk 70 also includes data files, device drivers, and other files.

Random Access Main Memory 90 also interfaces to computer bus 81 to provide CPU 80 with access to memory storage. In particular, when executing stored computer-executable process steps from disk 70 (or other storage media such as media accessed via floppy disk drive 71), CPU 80 loads those process steps from disk 70 to RAM 90 and executes the process steps out of RAM 90.

It should be noted that although computing equipment 65 illustrates a preferred embodiment of the present invention, the present invention also contemplates use of a dumb terminal directly connected to information bus 34, or other type of terminal accessing the system via Internet 55 or via another type of network connection.

II. Operation of Hardware and Software Architecture

A. Source Data Storage

Figure 9:
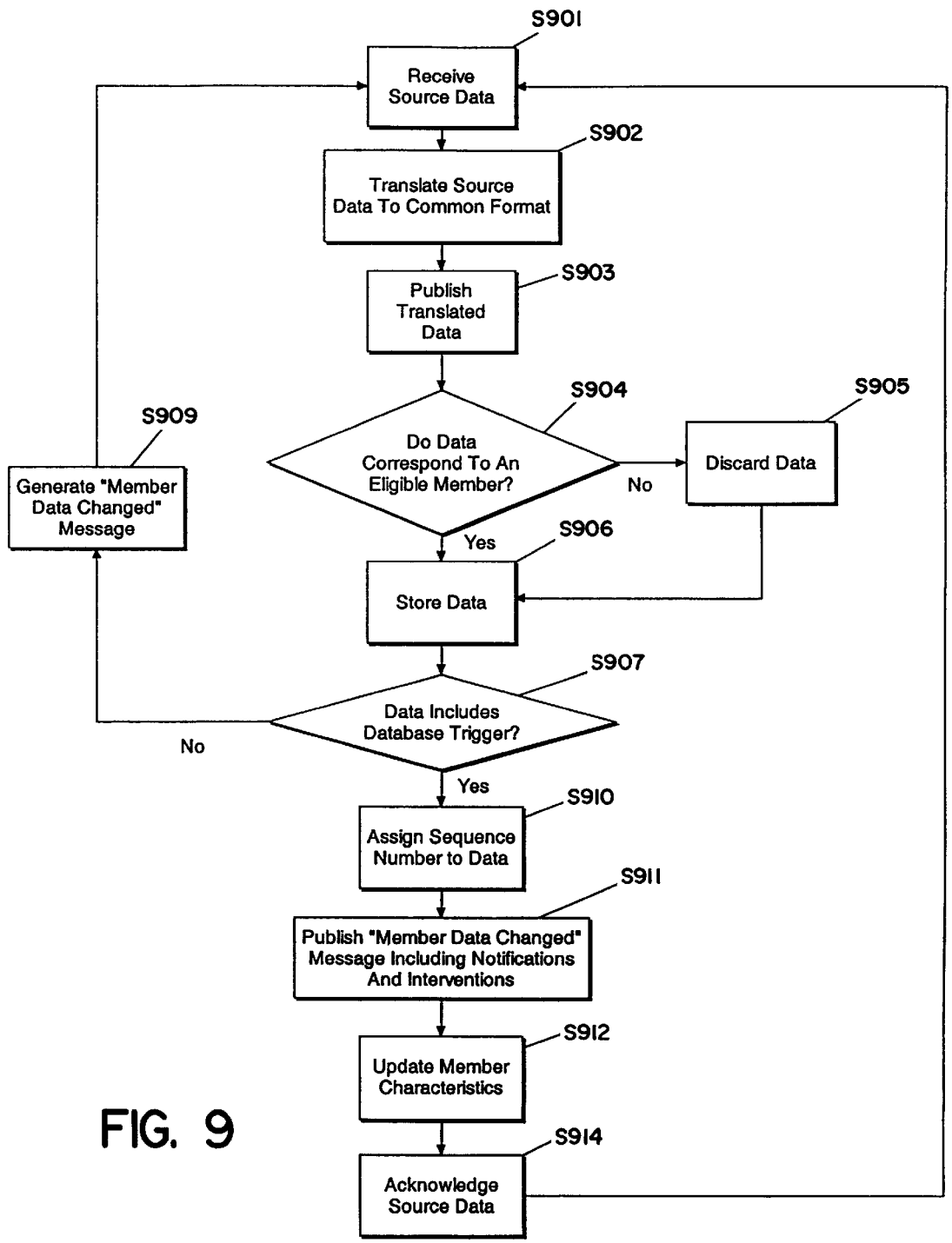
FIG. 9 is a flow diagram of process steps to obtain and to store data according to the present invention.

FIG. 9 is a flow diagram describing process steps executed by the FIG. 3 hardware and software architecture. Generally, the process steps are executed to receive source data, translate the source data to a common format, store the data, generate a notification based on the storage, and execute an intervention corresponding to the notification. The FIG. 9 process steps are preferably embodied in computer-executable code executed by microprocessors located within the system.

Specifically, the process steps begin at steps S901, wherein the system receives source data from source data files 30. As described above, source data files 30 can be received from various health care-related entities, and are usually in a legacy format unique to each entity. Accordingly, in step S902, the source data are translated by translator 31 to a common format for use in the system. In step S903, the translated data are published to information bus 34 using bus adapter 35a and API function calls to rendezvous daemon 36.

Figure 10:
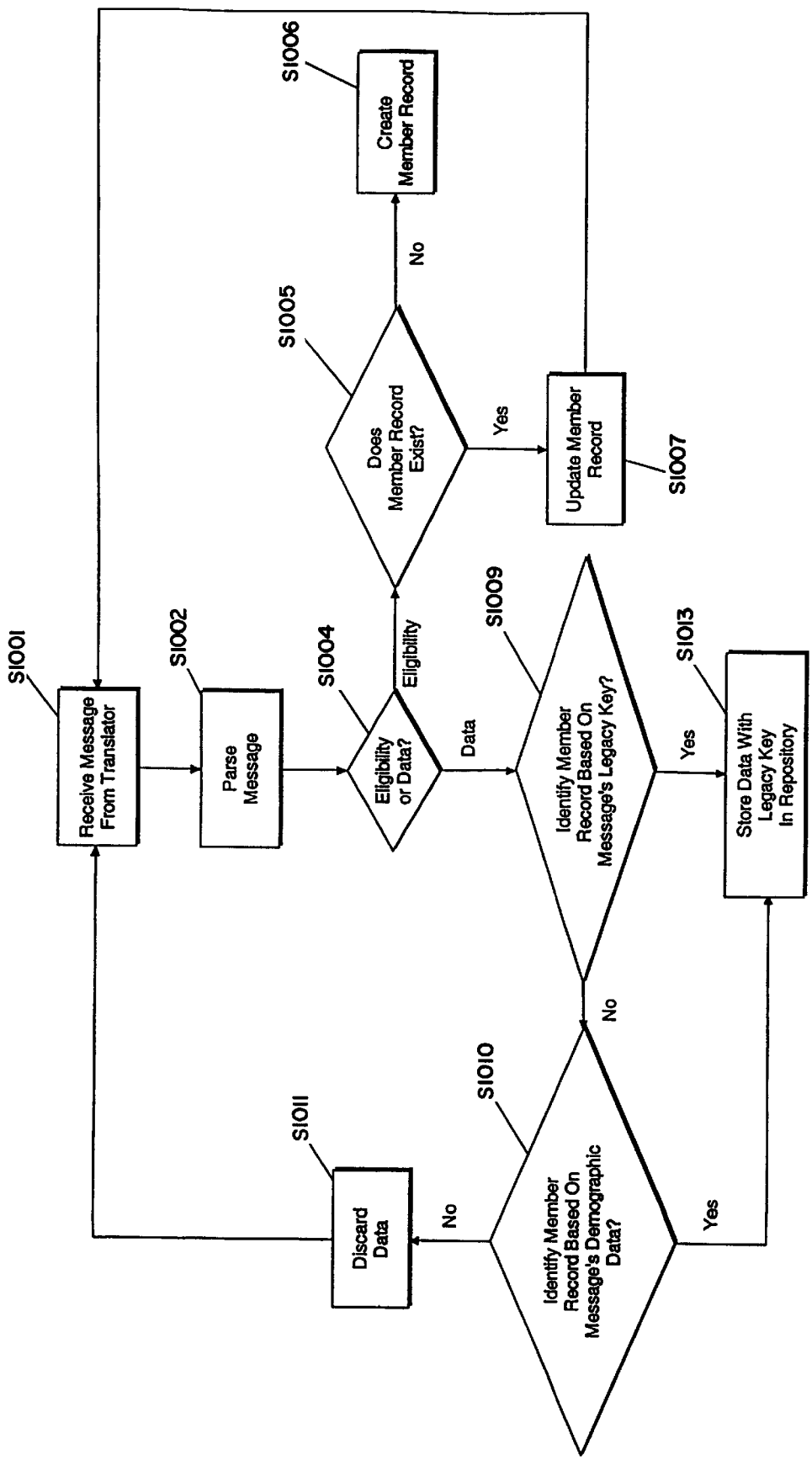
FIG. 10 is a detailed flow diagram of process steps to process and to store received source data according to the present invention.
Figure 11:
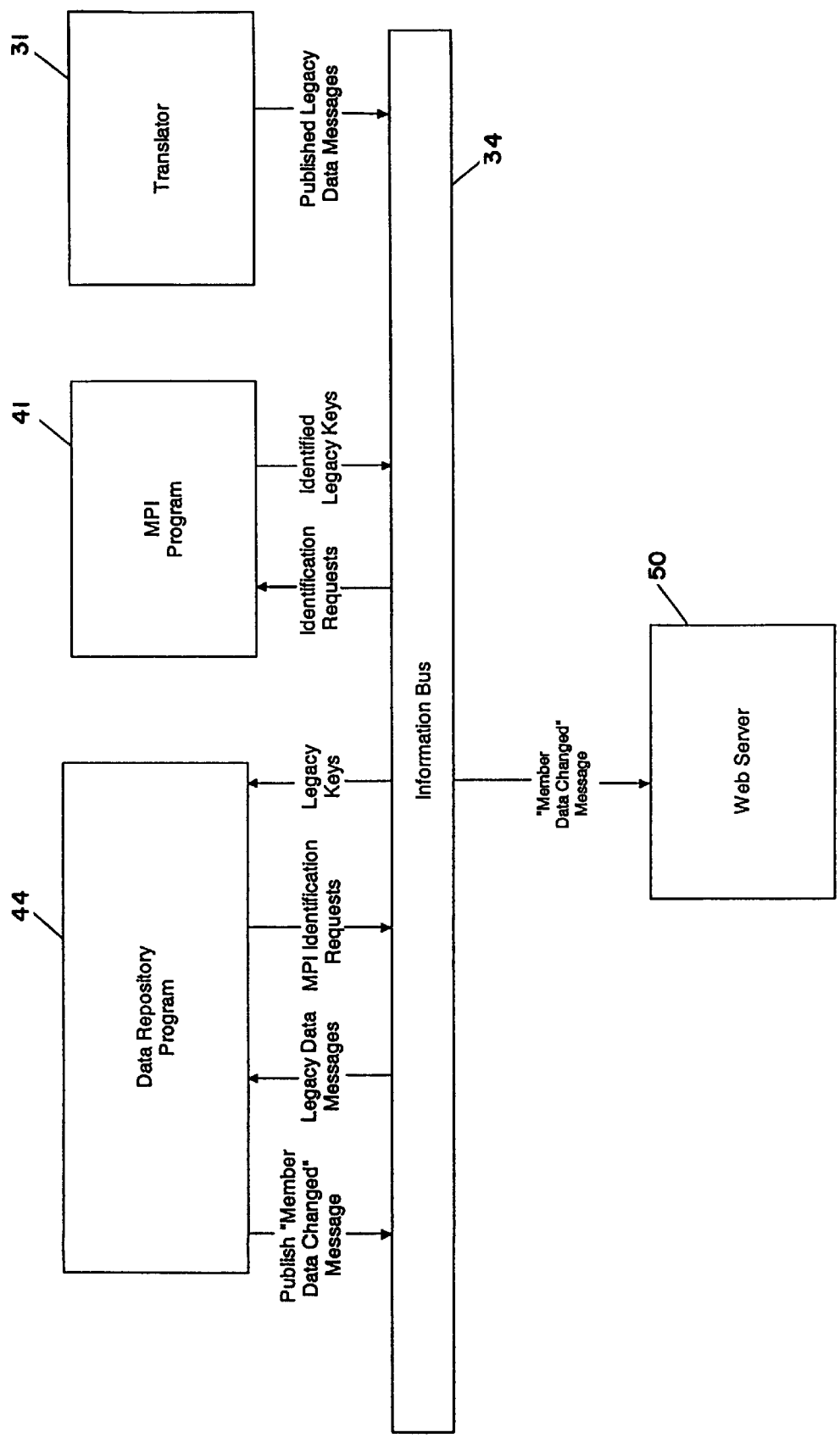
FIG. 11 is a block diagram illustrating the FIG. 10 process steps.

As mentioned, data repository program 44 subscribes to messages that contain data for storage in the system and to messages that contain request for stored data. Accordingly, data repository program 44 subscribes to all messages sent by translator 31. As a result, data repository program 44 obtains the data published in step S903. Next, in step S904, it is determined whether the translated data correspond to an eligible member. If not, flow proceeds to step S904, wherein the data are discarded. If so, flow proceeds to step S906, wherein the data are stored in data repository 42. FIGS. 10 and 11 illustrate in more detail the process of steps S904 to S906 and will be discussed below.

Remaining for the time being with the FIG. 9 process steps, data repository program 44 includes a list of database triggers and corresponding rules to execute in a case that a listed database trigger corresponds to data stored in data repository 42. For example, hospital admission 45 is a database trigger corresponding to the rule represented in FIG. 6. Accordingly, if, in step S907, it is determined that the data stored in step S906 describe a hospital admission, flow proceeds to step S910. If, in step S907, it is determined that the stored data do not describe a database trigger, flow proceeds to step S909. In step S909, data repository program 44 generates a Member Data Changed message, which is published via bus adapter 35b and rendezvous daemon 36. As described above, an application executing on web server 50 subscribes to such messages and stores the messages in web server database 51, from which the messages can be accessed via computing equipment 65.

In step S910, it has been determined that the data stored in step S906 describe a database trigger. Therefore, data repository program 44 stores a sequence number in data repository 42 along with the data stored in step S906. Next, in step S911, a Member Data Changed message is published, including a notification, intervention information, and the sequence number. Using the example shown in FIG. 6, storage of hospital admission data 45 in data repository 42 results in publication of a Member Data Changed message including notification 47 and intervention information 49 and a sequence/number corresponding to hospital admission data 45.

The Web Server Data Update Application executing out of web server 50 subscribes to the message published by data repository 42 and stores the message, notification, intervention information, and the sequence number in web server database 51. The sequence number is included in the message and is stored in database 51 so as to provide computing equipment 65 with a means to access the particular data stored in data repository 42 which resulted in the associated notification.

Next, in step S912, member characteristics stored in web server database 51 are updated according to the database trigger rules located in data repository program 44. With respect to FIG. 6, member characteristics 48 are updated in response to storage of hospital admission data 45 in data repository 42.

As described above, data repository program 44 may also generate clinical alert notifications, which can result from the detection of a database trigger and certain member characteristic, or from the detection of certain member characteristics only, without requiring storage of a database trigger. In either case, the prerequisites to rule execution preferably correspond to a risk situation.

In step S914, data repository program 44 publishes a message acknowledging the source data received in step S901 so that translator 31 is aware that the source data were processed.

By virtue of the foregoing process steps, heterogenous source data of a population of member patients can be stored in a database such that the data are easily accessible to a Coordination Specialist. Moreover, the above process steps alert a Coordination Specialist, or other user, regarding potential risk situations and provide the user with information and instructions to address the risk situation.

FIG. 10 is a detailed flow diagram of process steps S904 to S906 of FIG. 9. Flow begins in step S1001, in which a translated message of a particular type published by translator 31 is received by data repository program 44. The message type may be lab data, claims data, health plan data, or the like. Next, in step S1002, data repository program 44 executes a process specific to the message type and parses the message into a storable form.

In step S1004, it is determined whether the received message is an "eligibility" message containing a member record number or is simply a data message containing a legacy key. If the message is an eligibility message, flow proceeds to step S1005, where it is determined whether a member record corresponding to the eligibility message exists. In this regard, MPI program 41 searches MPI 40 for a member record having the member record number passed with the eligibility message.

If no such member record exists, flow proceeds to step S1006, wherein a member record is created in MPI 40 having the member record number passed with the eligibility message. Flow then returns to step S1001. Conversely, if it is determined in step S1005 that a member record having the member record number passed in the eligibility message exists in MPI 40, the member record is updated using information contained in the eligibility message, and flow returns to step S1001.

If, in step S1004, it is determined that the message received from translator 31 in step S1001 contains data, flow continues to step S1009. In step S1009, it is determined whether a member record exists in MPI 40 corresponding to the legacy key received with the data message. If the legacy key, which is used by the legacy system from which the data were obtained to identify a particular member, is not associated with a member record in MPI 40, flow proceeds to step S1010. In step S1010, demographic data stored in MPI 40 are compared with demographic data contained in the received data message to determine whether the message corresponds to any member record located in MPI 40. If the message does not correspond to any member record based on the demographic data, flow proceeds to step S1011, wherein the data are discarded or stored in a temporary storage database for a predetermined period of time.

If the identifications in step S1009 or step S1010 are successful, flow proceeds to step S1013, wherein the data are stored in data repository 42 along with the legacy key received with the data.

FIG. 11 is a block diagram illustrating several of the FIG. 10 process steps. In particular, FIG. 11 illustrates publication of legacy messages by translator 31 onto information bus 34 and reception of the legacy data messages by data repository 42. Next, in accordance with step S1009, data repository program 44 publishes an identification request for subscription by MPI program 41. Upon successful completion of either the step S1009 or step S1010 identifications, MPI program 41 publishes the identified legacy keys on information bus 34. The legacy keys are received by data repository program 44, which stores the legacy data messages along with the received legacy data keys in data repository 42. FIG. 11 also illustrates steps S909 and S911 of FIG. 9, wherein storage of legacy data in data repository 42 results in publication of a Member Data Changed message, and reception of the message by web server 50.

B. Data Retrieval

Figure 12:
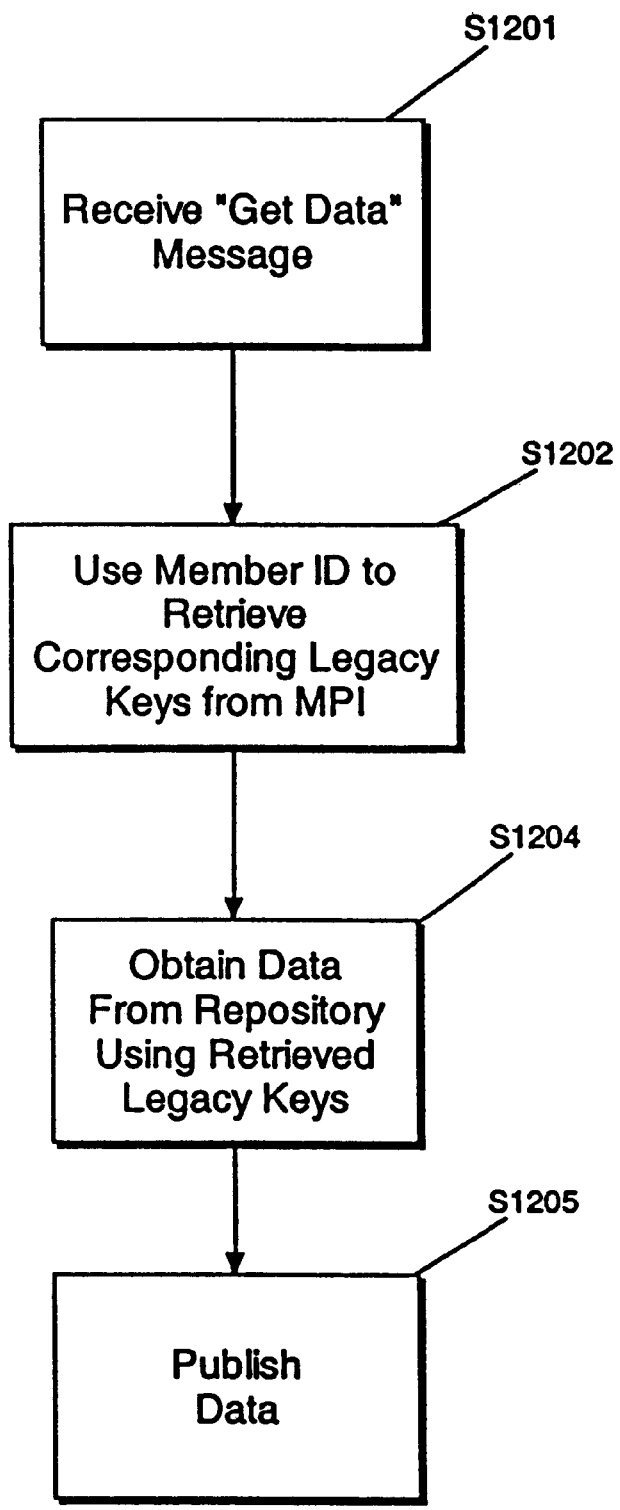
FIG. 12 is a flow diagram of process steps to obtain stored medical data according to the present invention.

FIG. 12 is a flow diagram of process steps to retrieve data from data repository 42. The process steps are preferably implemented by data repository program 44 in conjunction with bus adapter 35b and rendezvous daemon 36. In this regard, data repository 44 subscribes to Get Data messages published on information bus 34. Accordingly, in step S1201, data repository program 44 receives a Get Data message. It should be noted that the received Get Data message may be published by any entity on information bus 34, however, the present example assumes that the Get Data message is published by java proxy application 62, which is created on web server 50 due to a user logon to web server 50.

Included in the received Get Data message is a member ID. In step S1202, the member ID is published on information bus 34 along with a message to retrieve legacy keys corresponding to the member ID. MPI program 41 subscribes to the message and, also in step S1202, retrieves from MPI 40 all legacy keys corresponding to the member ID. Next, in step S1204, the retrieved legacy keys are used to obtain the requested data from data repository 42. For example, in a case that the Get Data message requested all claims data of a particular member, the retrieved legacy keys are used in conjunction with a table of claims data stored in data repository 42 to extract claims data particular to the subject member.

Flow continues from step S1204 to step S1205, wherein the requested data are published on information bus 34, picked up by web server 50, and delivered to the requesting application.

Figure 13:
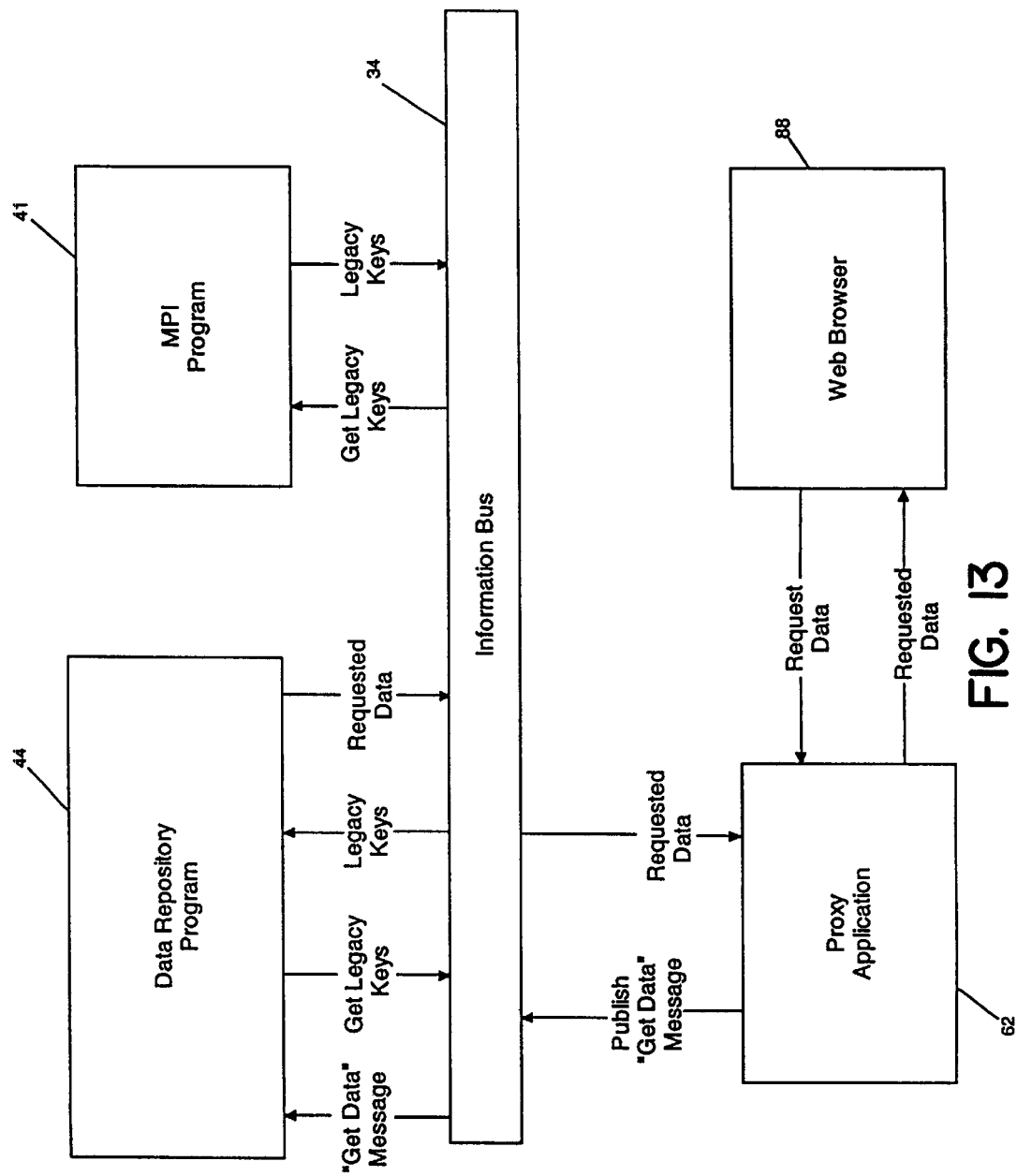
FIG. 13 is a block diagram illustrating the FIG. 12 process steps.

FIG. 13 is a block diagram illustrating the process steps of FIG. 12. In particular, FIG. 13 shows web browser 88 issuing a request for data to web server 50. In response, proxy application 62 publishes a Get Data message to information bus 34. The Get Data message is subscribed to by data repository program 44, which requests legacy keys from MPI 40 based on a member ID contained in the Get Data message. MPI program 41 locates all legacy keys corresponding to the member ID and passes the legacy keys to information bus 34, from which they are retrieved by data repository program 44. The retrieved legacy keys are used to obtain the requested data from an appropriate data table, and the requested data are then published on information bus 34, from which they are retrieved by proxy application 62 for transfer to web browser 88. By virtue of the foregoing process steps, legacy data can be obtained from data repository 42 without requiring knowledge of legacy keys.

Similarly, in order to store data from web browser 88 to data repository 42, proxy application 62 issues a Set Data message including the particular data and a corresponding member ID. Data repository program 44 subscribes to the Set Data message and therefore obtains the message and stores the data in an appropriate table of data repository 42 along with the member ID. It should be noted that, as described above with respect to step S907 of FIG. 9, the data stored in data repository 42 as a result of a Set Data message may cause generation of a notification.

C. Web Page Creation

Figure 14:
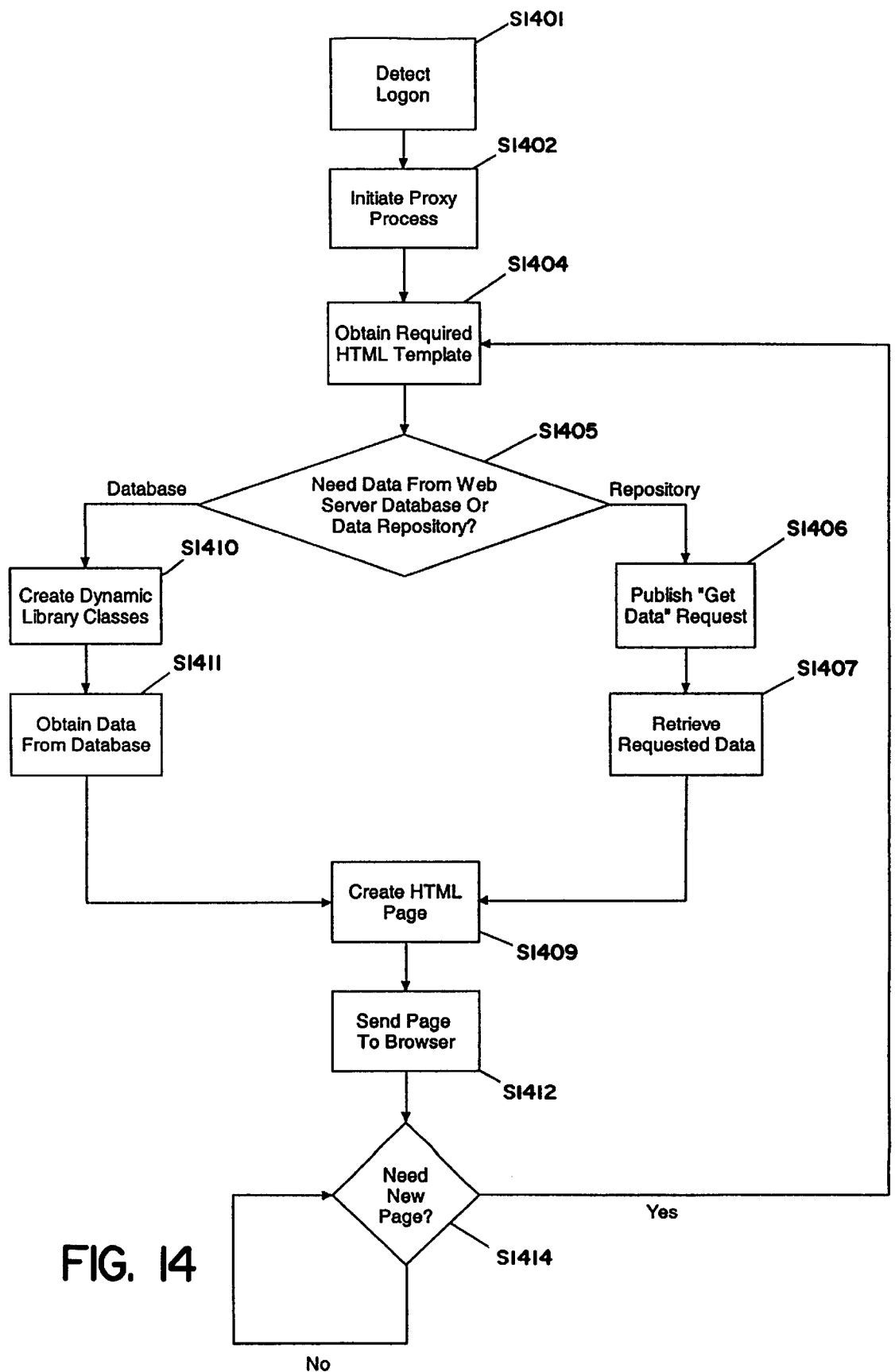
FIG. 14 is a flow diagram of process steps to create and deliver HTML pages according to the present invention.

FIG. 14 is a flow diagram describing process steps executed by the system to deliver HTML pages and java applets to a user of computing equipment 65. Flow begins at step S1401, at which point a user has accessed a logon HTML page presented by web server 50 over Internet 55 and has properly logged onto the system. Upon detecting the logon, flow proceeds to step S1402, wherein web server 50 initiates java proxy application 62. Next, in step S1404, interaction manager 57 of web client service 54 obtains an initial menu HTML template from HTML templates 58. It should be noted that most of HTML templates 58 do not represent complete web pages, but require additional data prior to delivery to computing equipment 65. In this regard, in step S1405, it is determined whether data required by the obtained HTML template are located in web server database 51 or in data repository 42. If the required data are located in data repository 42, flow proceeds to step S1406, wherein java proxy application 62 publishes a Get Data request via bus adapter 35e and rendezvous daemon 36. Next, by virtue of the process steps of FIG. 10, illustrated in FIG. 11, the requested data are retrieved in step S1407. Flow then continues to step S1409, wherein an HTML page is constructed using the HTML template and the requested data.

If, in step S1405, it is determined that the data required for completion of the HTML template are located in web server database 51, flow proceeds to step S1410. In step S1410, appropriate dynamic library classes from dynamic libraries 60 are created to extract the required data from web server database 51. Accordingly, in step S1411, the classes are used to obtain the required data from web server database 51. It should be noted that the required data may include java applets stored in database 51. Flow continues from step S1411 to step S1409, wherein the HTML template is completed using the obtained data. Of course, data for a single HTML page may be obtained from both web server 51 and data repository 42, in which case steps S1406, S1407, S1410 and S1411 are executed with respect to the single page.

After creating the HTML page in step S1409, the page is sent, in step S1412, via Internet 55 to World Wide Web browser 88 executing in computing equipment 65. Then, based on user interaction with World Wide Web browser 88, it is determined in step S1414 whether a new HTML page is required. If not required, flow pauses at step S1414. If so, flow returns to step S1404 wherein a HTML template corresponding to the new page is retrieved from HTML template 58 and flow continues as described above.

On a related note, the present invention also enables data storage in data repository 42 and web server database 51 through interaction with World Wide Web browser 88. In this regard, in a case that user interaction with browser 88 indicates that data are to be stored in the system, it is determined whether the data should be stored in web server database 51 or data repository 42. For data to be stored in web server database 51, interaction manager 57 creates dynamic library classes from dynamic libraries 60 to store the data and the data are stored by the created dynamic library classes. For data to be stored in data repository 42, Java proxy application 62 publishes a Set Data message to which data repository program 44 subscribes and based on which the data are stored in data repository 42.

III. Clinical Uses of System
A. Member Monitoring and Management

The above-described hardware, software, and operation thereof are preferably used to monitor and manage the health care of a patient population. The following is a description of a preferred embodiment of web client service 54 which provides such functionality.

Generally, web client service 54 provides a user with a comprehensive set of web pages in which data stored in the system are displayed for evaluation and manipulation. Moreover, the preferred embodiment of web client service 54 also offers features such as automatic reminder letter generation, automatic follow-up reminders, physician paging, or the like. Therefore, web client service 54, in conjunction with the other elements of the system, allows a user to proactively address potential health care process failures and/or unintended health care utilization by notifying a user of detected risk situations and by providing information and -resources to the user, thereby enabling the user to address the risk situation. As described above, such information preferably includes SOPs designed to address detected risk situations.

Figure 15:
FIG. 15 is a view of a Home page for use in conjunction with the present invention.

Initially, a user inputs a universal resource locator (URL) into web browser 88 executing in computing equipment 65. The URL is then sent to the World Wide Web via connection 72 and, using standard Internet protocols, a home page corresponding to the URL is received from the Internet via connection 72. FIG. 15 shows a sample home page for use in the present system. Once retrieved, the home page is displayed on display 66 of computing equipment 65.

Within web client service 54, as described above, interaction manager 57 receives a request from browser 88 and, in response, creates Home page 100 using a template from HTML templates 58. Since no data are required from database 51 or from data repository 42 in order to complete Home page 100, the template is merely sent to computing equipment 65 via Internet 55. Upon viewing Home page 100, a user completes User Name field 102 and Password field 104 in order to obtain access to the system.

It should be noted that the system is preferably used by a Coordination Specialist, a provider, a Case Manager, or a System Administrator. A Case Manager is a user assigned to deal with a specific aspect of member health care, while a System Administrator is intended to monitor the general operations of the entire system and therefore requires access to all data on the system.

Preferably, the system also allows providers "read-only" access to certain system information, so as to allow effective diagnosis and treatment and so as to ensure that only a user in charge of a particular member can manipulate stored information corresponding to that member. Such a protocol is believed to likely reduce communication errors in management of patient health care. Of course, certain provider-specific pages can be provided to allow provider input and manipulation of system data. Such pages can be used to display notification information intended for receipt by a provider, as discussed above.

Figure 16:
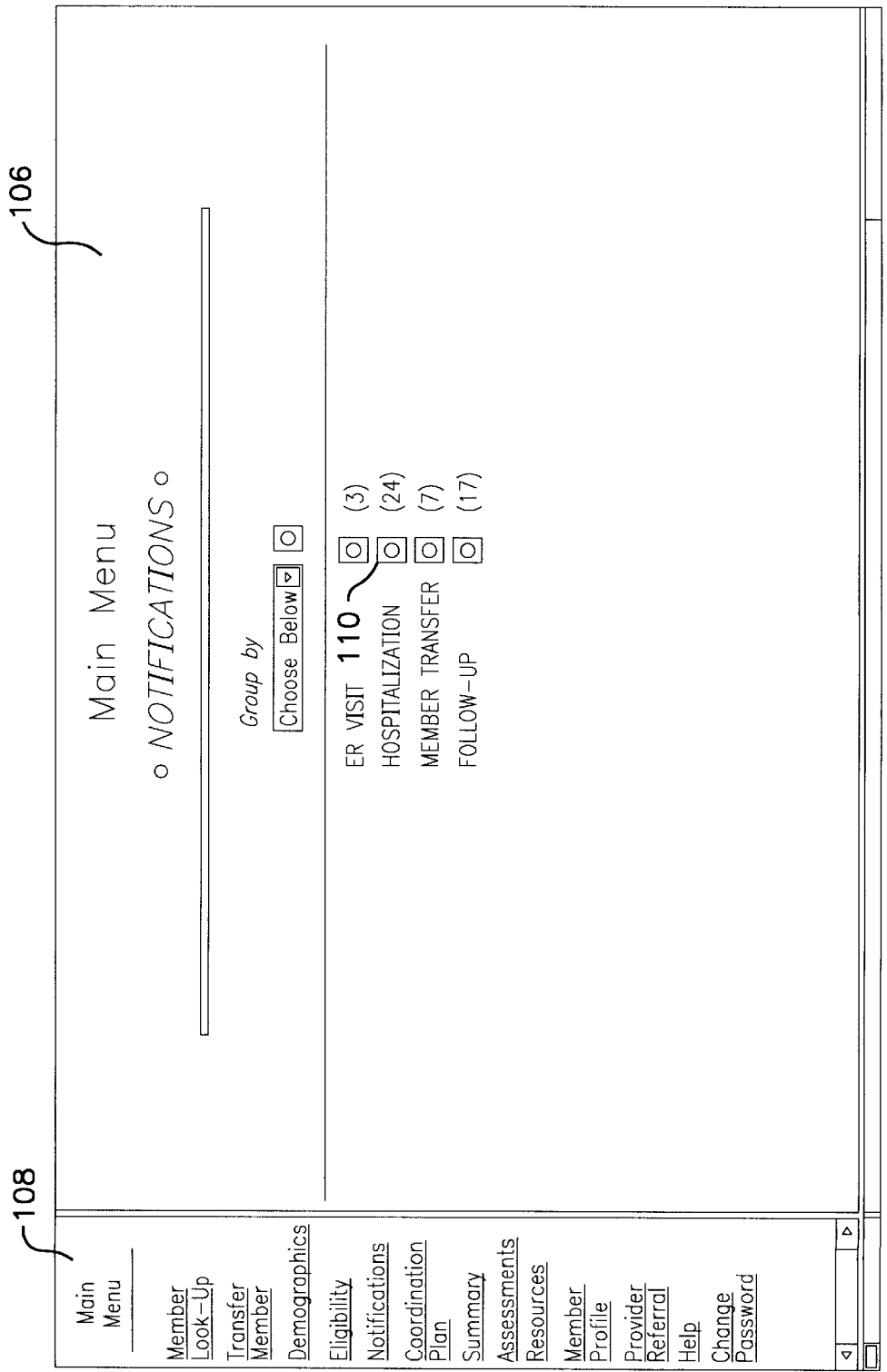
FIG. 16 is a view of a Main Menu page and a Main Menu frame for use in conjunction with the present invention.

After submitting logon information by selecting sign-in icon 105, web client service 54 checks the submitted information against web server database 51 and creates Main Menu page 106, shown in FIG. 16. Construction of page 106 proceeds along the lines described above with respect to steps S1404 to S1409 of FIG. 14. As shown, page 106 lists notifications which have been generated by the system and stored in web server database 51 and indicates how many of each of the displayed types of notifications have been received. The notifications may be listed alphabetically or based on a priority which is associated with the notification in web server database 51. Page 106 also includes Main Menu frame 108, which lists other pages and other frames accessible by selecting the appropriate title in frame 108.

As shown in FIG. 16, notifications can be generated based on a detected medical event, such as a hospitalization, or on an item input to the system such as a member transfer or a scheduled follow-up. Notifications may also be generated based on a clinical alert or on an analysis of assessment data. Assessments and analysis thereof will be described below.

The HTML pages provided by web client service 54 will be described below assuming use by a Coordination Specialist. Accordingly, page 106 displays notifications corresponding to members managed by a logged-on Coordination Specialist. In order to do so, web server database 51 includes lists of Coordination Specialists and corresponding members, which are accessed in order to extract proper notification information from web server database 51 to create page 106. Moreover, the displayed notifications are those intended for receipt by the logged-on Coordination Specialist, rather than those associated with a Case Manager or other user in web server database 51.

Figure 17:
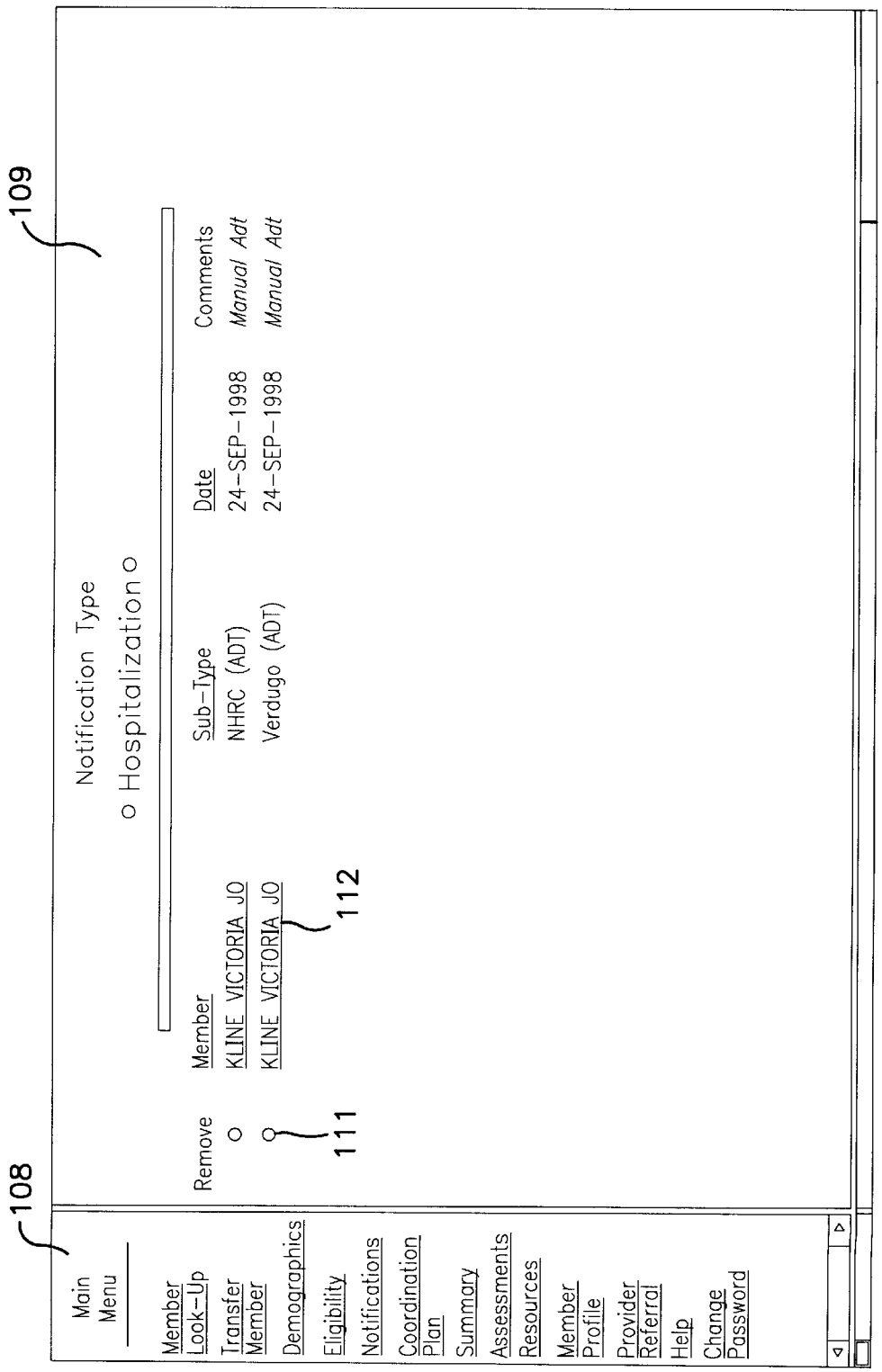
FIG. 17 is a view of a Notification Type page and a Main Menu frame for use in conjunction with the present invention.

FIG. 17 shows web page 109, which is created upon selection of Hospitalization icon 110 of page 106. In order to build page 109, web client service 54 accesses data repository 42 using the steps described in FIG. 14. As shown in FIG. 17, frame 108 does not change upon selection of icon 110, so as to enable a Coordination Specialist to access the page or frames listed therein.

Using sequence numbers stored along with the displayed notifications in web server database 51, web client service 54 obtains data for display in Notification Type page 109. After completing interventions corresponding to a displayed notification, the Coordination Specialist can remove the displayed notification, thereby deleting the notification from a list of current notifications stored in database 51, by selecting corresponding icon 111.

The Coordination Specialist then selects member 112 to obtain details on the corresponding notification. Accordingly, Notification Details page 114 is created by web client service 54 and sent to computing equipment 65. FIG. 18 shows Notification Details page 114, which displays data stored in data repository 42 which triggered a selected notification. The data is accessed, as described above, using a sequence number stored with the selected notification. As shown, the data indicates that the displayed member was hospitalized on Jul. 21, 1998 for pneumonia.

Preferably, the Coordination Specialist next checks member eligibility to confirm the member's health care coverage. Eligibility is checked by selecting "Eligibility" 115 in frame 108. Such selection is transferred to web client service 54 through interaction manager 57, wherein the member ID of the subject member is used to obtain corresponding eligibility information from data repository 42. Using the eligibility information and an appropriate template from HTML templates 58, service 54 constructs Eligibility page 117, shown in FIG. 19.

After confirming eligibility, a Coordination Specialist preferably selects "Demographics" 118 from FIG. 19. In response to this selection, Demographics page 120 of FIG. 20 is created using an appropriate template and demographics information stored in MPI 40, as illustrated in FIG. 4. It should be noted that such demographics information is provided by a health plan in a preferred embodiment, and cannot be directly edited by a Coordination Specialist. Accordingly, the Coordination Specialist can select "Edit Demographics" 122 in order to access Edit Demographics page 123, shown in FIG. 21.

Edit Demographics page 123 displays the demographics information displayed in Demographics page 120 as well as demographics information obtained from other sources by the Coordination Specialist. Such demographics information is stored in conjunction with the subject member ID in web server database 51 such that the information can be updated and accessed quickly. Accordingly, Edit Demographics page 123 allows a Coordination Specialist to ensure that the data displayed in Demographics page 120 are correct.

In order to obtain a more complete picture of the subject member, a Coordination Specialist may then select "Member Profile" 125 from frame 108. As a result, web client service 54 creates Member Profile page 126 of FIG. 22, which provides a snapshot of relevant data taken from the system. For example, Member Profile page 126 may include diagnosis information gleaned from an analysis of a risk survey and/or claims data, information as to whether the member has been delegated to a care partner, such as a disease management company, and a description of clinical alerts associated with the member. Member Profile page 126 also includes lists of problems and goals of the member, which are determined from member assessments, and information regarding interventions and community resources relating to the member.

Figure 23:
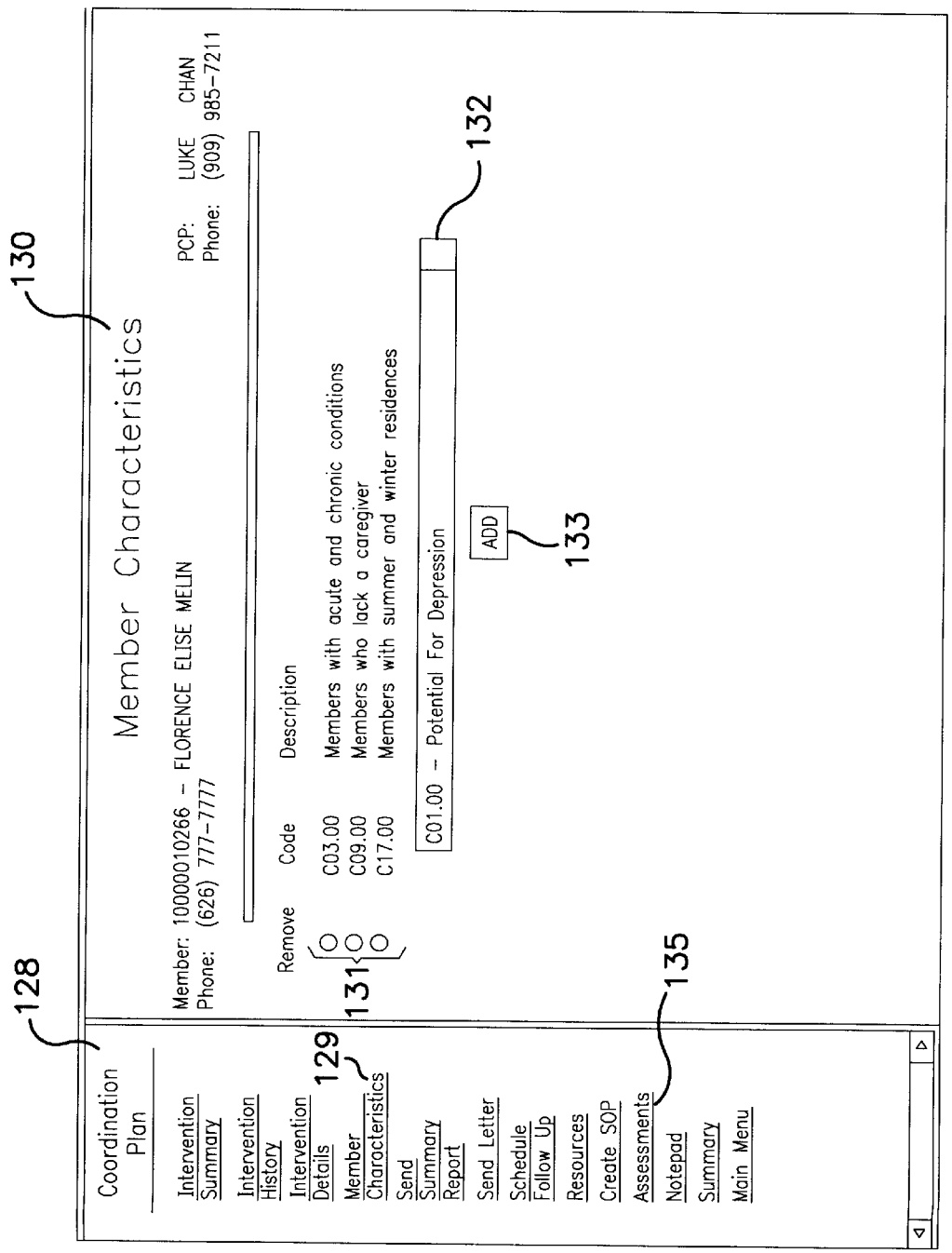
FIG. 23 is a view of a Member Characteristics page and a Coordination Plan frame for use in conjunction with the present invention.

Next, upon selecting "Coordination Plan" 127 from frame 108, Coordination Plan frame 128 of FIG. 23 is substituted for Main Menu frame 108. Also shown in FIG. 23 is Member Characteristics page 130, which is displayed upon selection of "Member Characteristics" 129 of Coordination Plan frame 128.

Upon selection of "Member Characteristics" 129, web client service 54 accesses a list of member characteristics corresponding to the subject member and stored in web server database 51. In order to do so, web client service 54 performs the above-described steps S1410 and S1411 of FIG. 14. Next, according to steps S1409, Member Characteristics page 130 is created and sent to computing equipment 65. As shown in FIG. 23, Member Characteristics page 130 displays icons 131 which can be selected in order to remove a corresponding member characteristic from the member characteristics list in web server database 51. In addition, member characteristics may be selected using pull-down button 132 and added to the member characteristics list by way of "ADD" icon 133.

Figure 24:
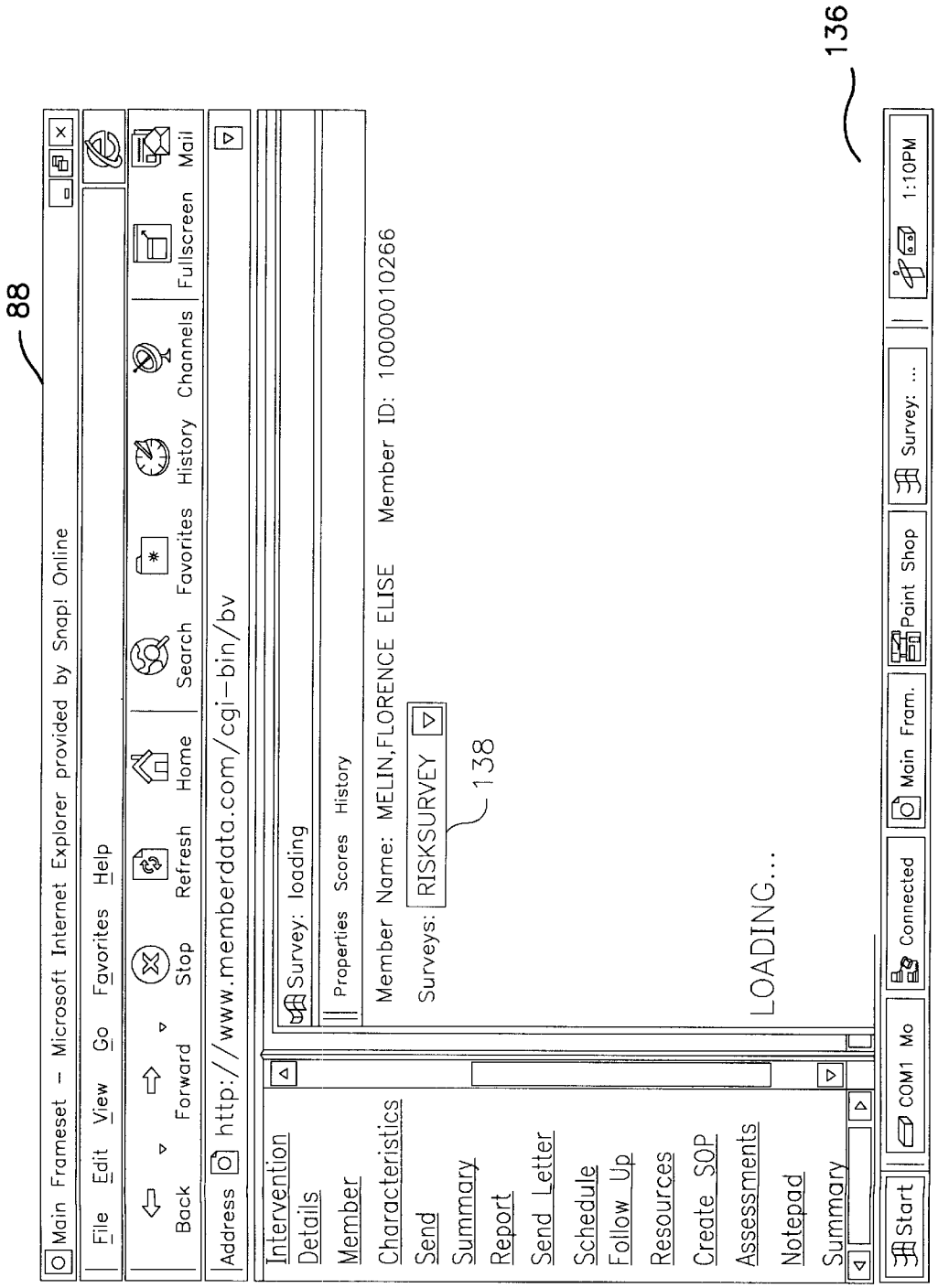
FIG. 24 is a view of a World Wide Web browser display and a java applet window in accordance with the present invention.

Further information of the subject member can be obtained by selecting "Assessments" 135 in Coordination Plan frame 126. FIG. 24 is a view of display screen 66 upon selection of "Assessments" 135. As shown, window 136 opens as a window separate from executing browser 88. It should be noted that the window is a java applet window. Accordingly, upon selection of "Assessments" 135, a corresponding java applet is retrieved from web server database 51 and downloaded through Internet 55. Survey input area 138 allows user selection of either "RISK SURVEY", which corresponds to an initial survey completed by the member, or "ASSESSMENTS", which are other assessments contained within the system. As shown in FIG. 24, "RISK SURVEY" has been selected. Accordingly, java proxy application 52 receives a request for a member risk survey and obtains the risk survey from data repository 42 using the process of FIG. 13 and FIG. 14.

Figure 25:
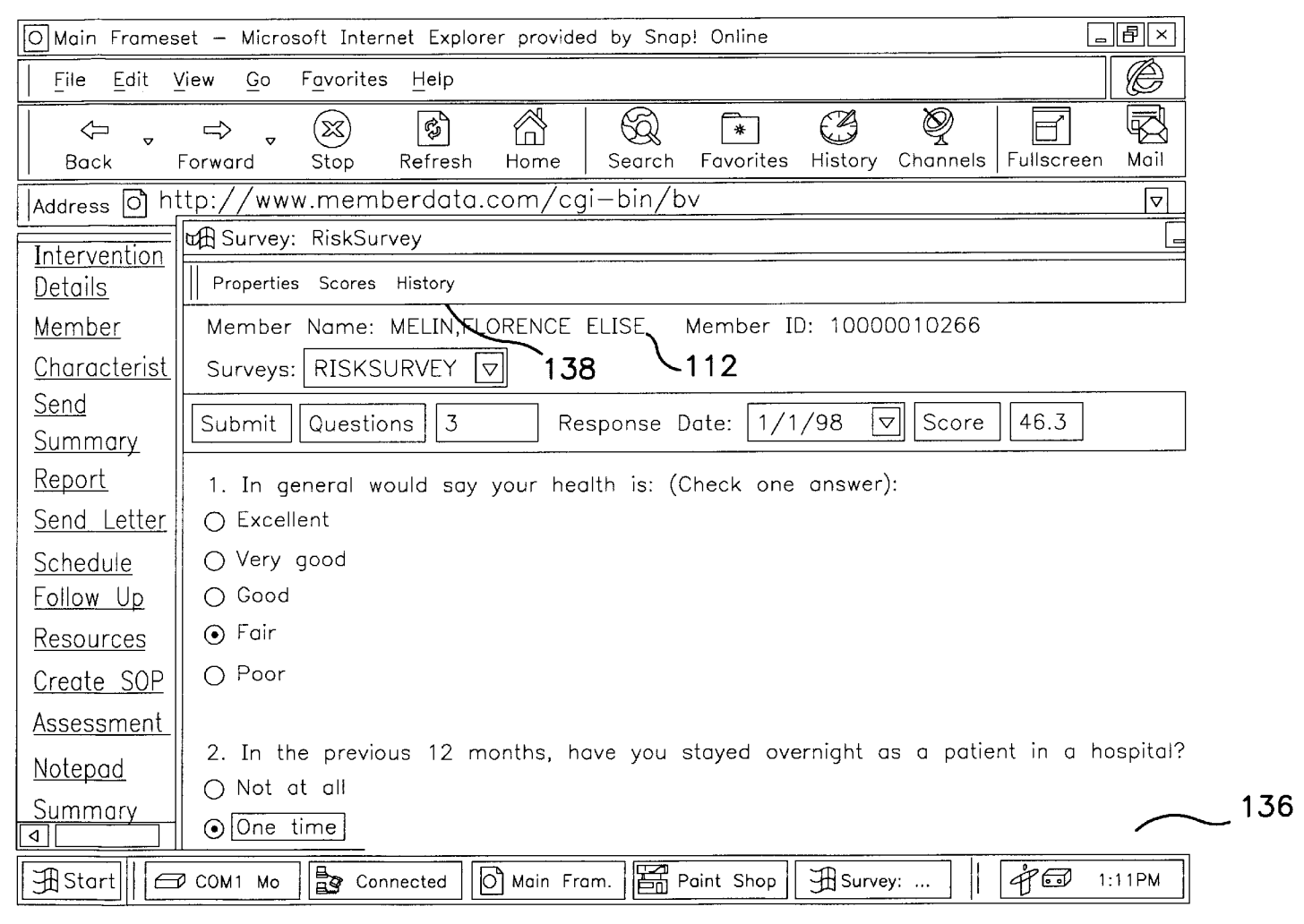

FIG. 25 shows applet window 136 after the risk survey has been received from data repository 42 and delivered to computing equipment 65. As shown, applet window 136 displays questions and answers of a subject member risk survey completed on Jan. 1, 1998, along with a corresponding score. Alternatively, a Coordination Specialist can complete a new risk survey with a corresponding new response date associated with the member, which can be submitted to the system and stored in data repository 42. Accordingly, either the initial or the new risk survey can be subsequently retrieved based on the corresponding response date.

Figure 26:
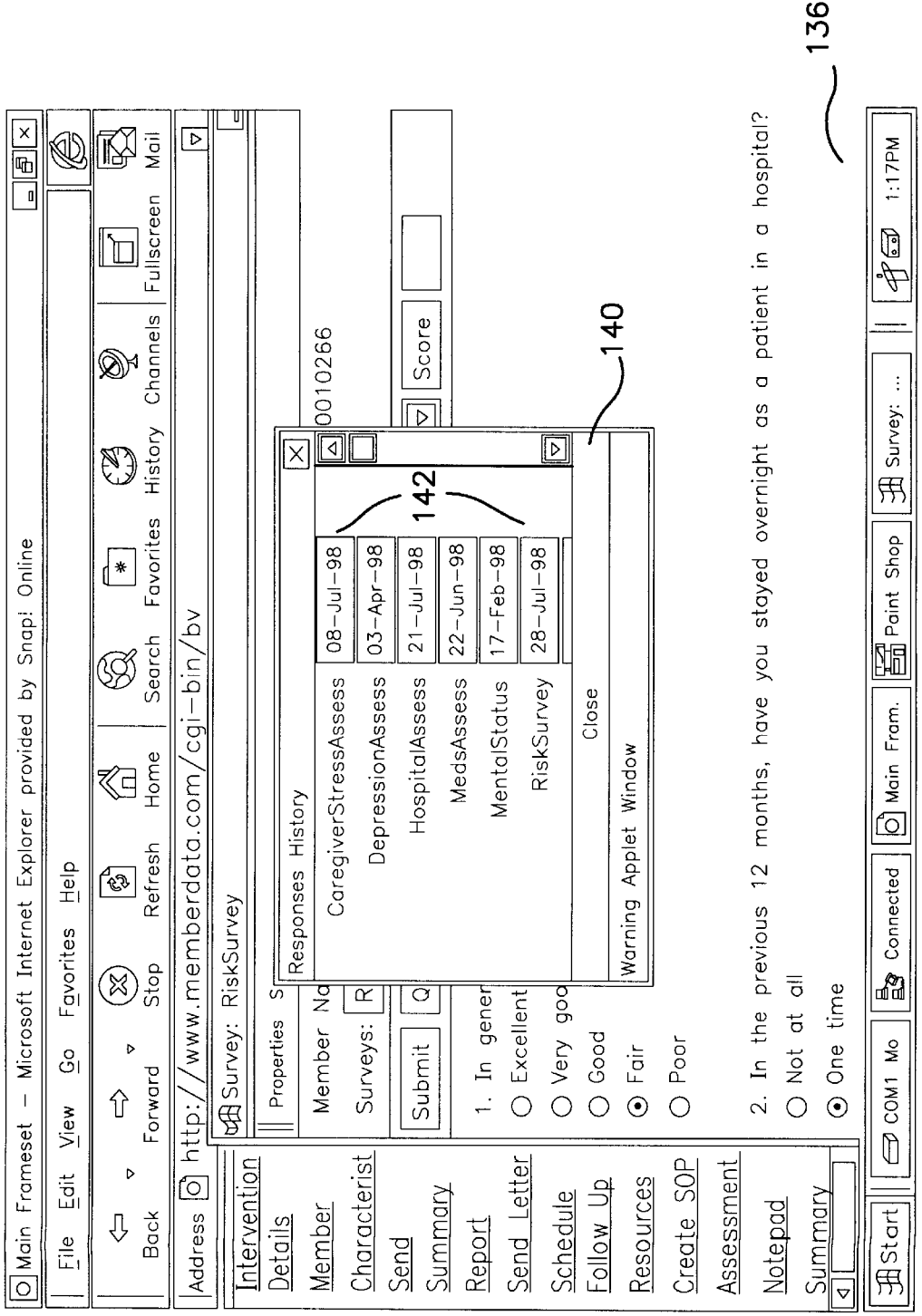
FIG. 26 is a view of a World Wide Web browser display and two java applet windows in accordance with the present invention.

FIG. 26 shows Response History applet window 140, which is displayed upon selection of "History" 138 in window 136. In response to the selection, java proxy application 62 obtains response history data from web server database 51 corresponding to various assessments and delivers the data to applet window 140. Icons 142 may then be selected to retrieve the corresponding assessments.

The java applets used to provide assessment functionality also preferably provide pop-up windows through which a user may transmit a stored assessment via facsimile. Moreover, the applets preferably provide pop-up windows through which pharmaceutical information can be obtained.

It should be noted that the assessment applets are not used merely to review member responses in an attempt to obtain additional medical information. To the contrary, assessments are often required elements of interventions corresponding to particular notifications. In addition, assessment scores, as well as individual responses to particular assessment questions become data stored by the system and therefore subjectable to analysis using techniques similar to those described with respect to clinical alerts.

That is, a program executing on web server 50 may trigger a second assessment based solely on a member's score on a first assessment, based solely on particular responses to the first assessment, based solely on detected member data, including member characteristics, claims data or the like, based solely on detected medical events, or based on any combination of the foregoing. Therefore, the assessments of the present invention are preferably fully integrated with the system so as to be triggered by received data, to identify problems and goals, to cause generation of notifications and corresponding interventions, and to cause updating of member characteristics or other data in the system.

Even more information regarding a member can be obtained by selecting "Intervention History" in Coordination Plan frame 128. As described above, an intervention history is stored in web server database 51 along with a subject member ID. Accordingly, web client service 54 obtains an intervention history from web server database 51 using dynamic libraries 60 and creates Intervention History page 145, shown in FIG. 27, using HTML templates 58.

As shown, Intervention History page 145 displays data corresponding to previous interventions performed with respect to a subject member. Page 145 also includes "Undo" buttons, which can be used to delete any intervention listed on page 145 that day. As a result, the deleted intervention will be displayed on an Intervention Summary page, to be described below. Advantageously, such a feature maintains data integrity within the system while allowing Coordination Specialists to correct recently-made mistakes.

Figure 28:
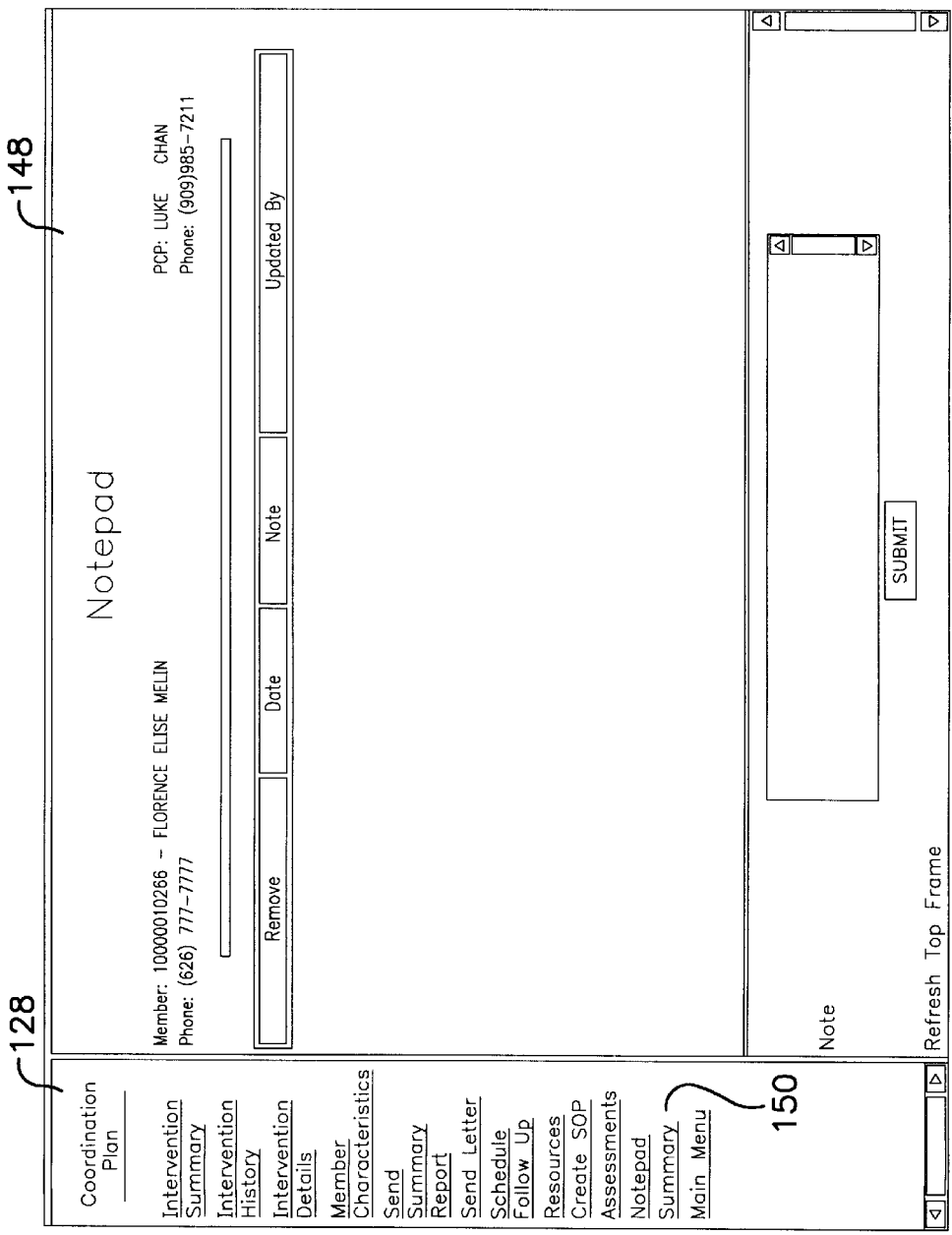
FIG. 28 is a view of a Notepad page and a Coordination Plan frame for use in conjunction with the present invention.

Additional member information can be obtained or recorded by selecting "Notepad" 146 in Coordination Plan frame 128. Similar to creation of Intervention History page 145, Notepad page 148, shown in FIG. 28, is created using HTML templates 58 and notepad-related information stored in web server database 51 in conjunction with the subject member ID. In the case shown in FIG. 28, no notepad information has been stored in web server database 51 with respect to the subject member.

Figure 29:
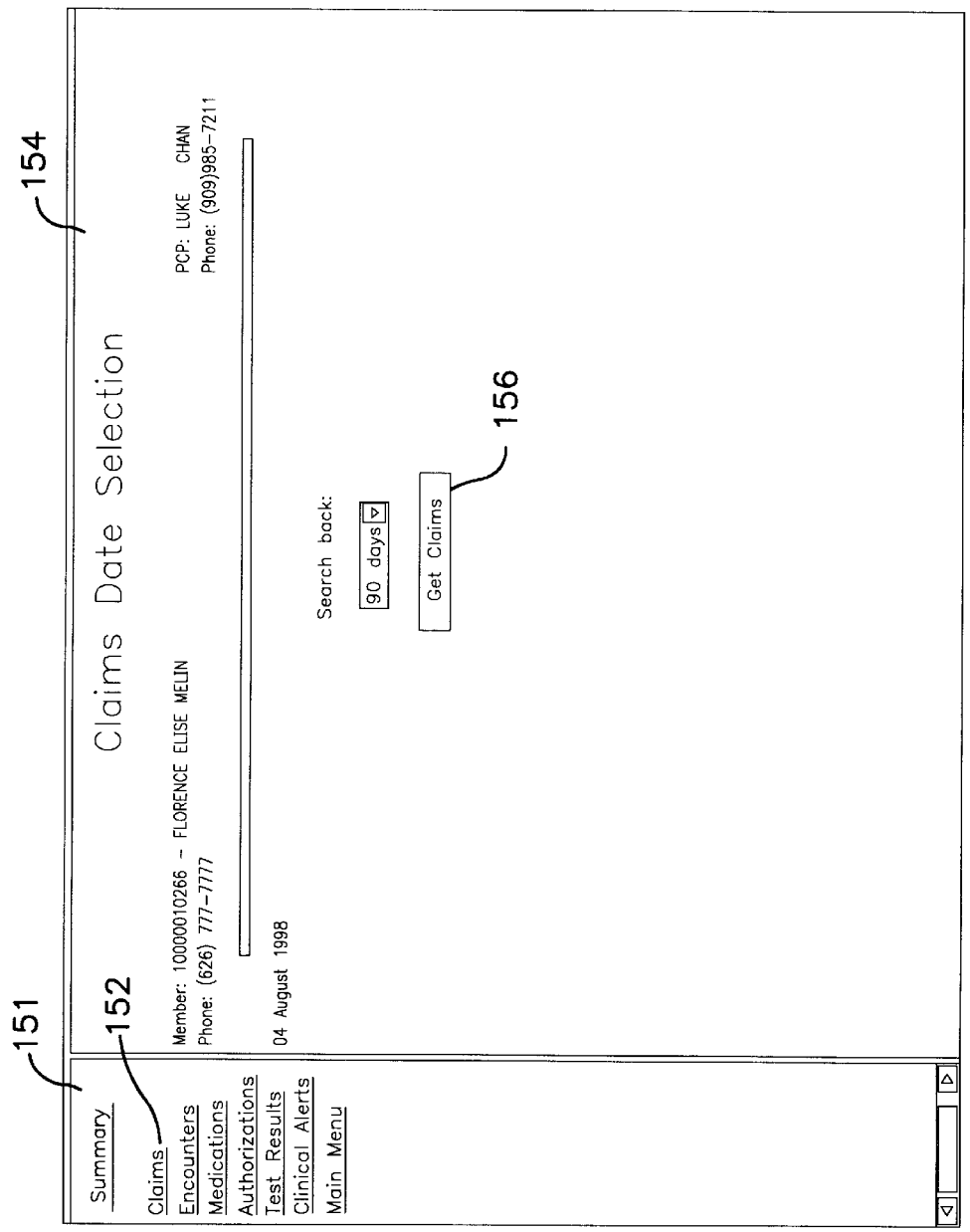
FIG. 29 is a view of a Claims Date Selection page and a Summary frame for use in conjunction with the present invention.

Member information is also available through "Summary" 150 of Coordination Plan frame 126. FIG. 29 shows Summary frame 151 upon selection of "Claims" 152. Due to such selection, Claims Date Selection page 154 is constructed and sent to web browser 88. Using Claims Date Selection page 154, a Coordination Specialist can retrieve medical claims data stored during a previous range of time.

Upon selecting Get Claims icon 156, Claims page 157, shown in FIG. 30, is constructed and sent to web browser 88. Claims page 157 includes a template from HTML templates 58, as well as claims data retrieved by web client service 54 from data repository 42 using the member ID of subject member 112 and the relationships stored in MPI 40. Similarly, FIG. 31 shows Medications page 158, which is created and displayed upon selection of "Medications" 160 from Summary frame 151. Again, web client service 54 constructs Medications page 158 using HTML templates 58, a member ID of the subject member, data repository 42, and MPI 40, as described in FIG. 14.

It should be noted that "Encounters", "Authorizations", and "Test Results" pages available through Summary frame 151 also display, respectively, medical group encounter data, insurance authorization data, and laboratory test result data stored over a specified period. Such data are also obtained by web client service 54 and delivered to web browser 88 as described above with respect to pages 157 and 158.

Also available from Summary frame 151 is "Clinical Alerts" 161, which provides access to a Clinical Alerts Date Selection Page and a Clinical Alerts Page similar to those described above with respect to Claims data.

Figure 32:
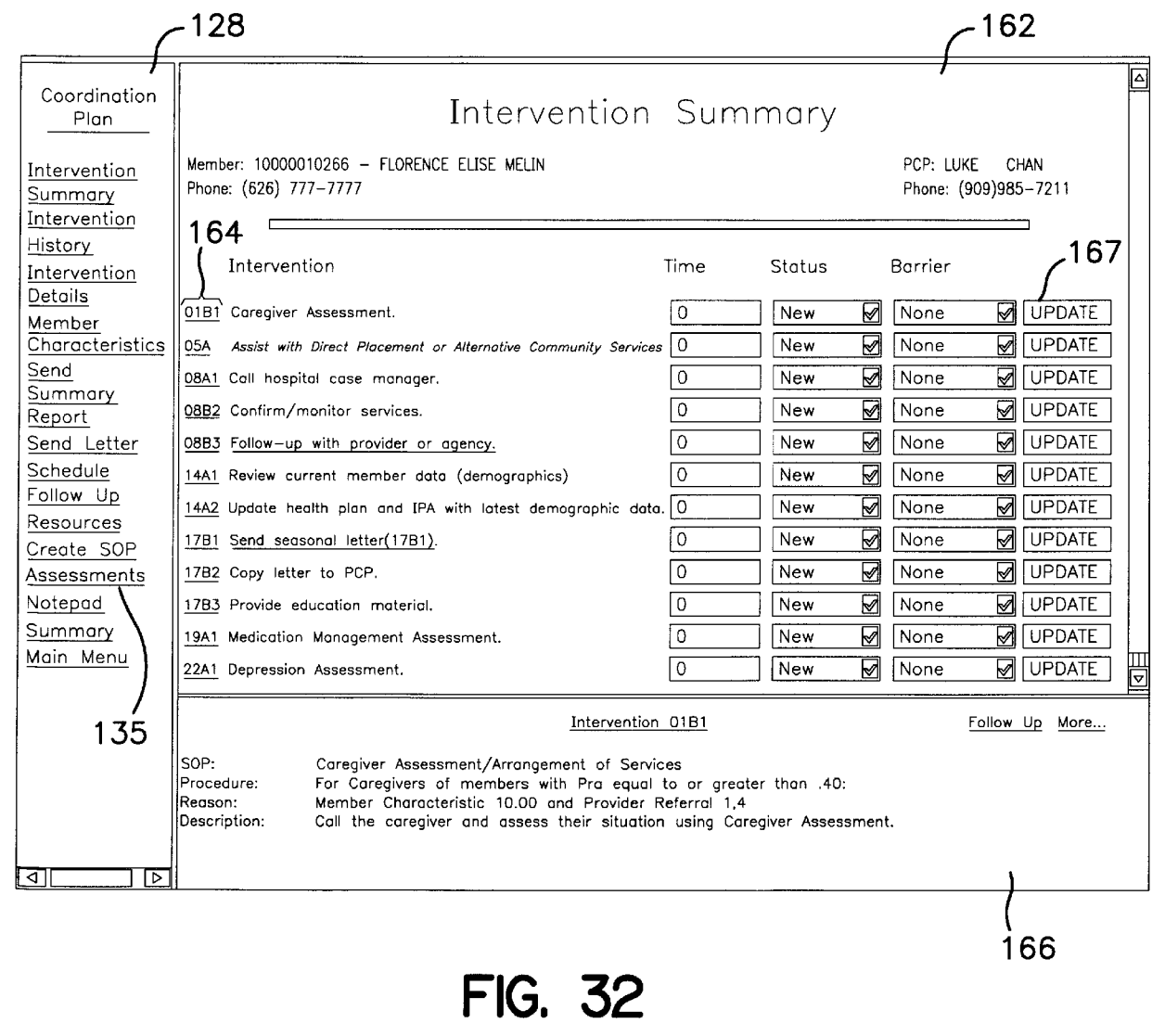

FIG. 32 shows Intervention Summary page 162, which is accessible by selection of "Intervention Summary" 165 from Coordination Plan frame 128. Intervention Summary page 162 lists interventions associated with the notification selected in Notification Type page 109 of FIG. 17. In this regard, the interventions listed in Interventions Summary page 162 are those published and stored in database 51 along with the selected notification according to a rule such as that illustrated in FIG. 6. Preferably, only intervention codes are published and stored along with the selected notification in web server database 51, and those codes are compared to data in an intervention table stored in database 51 to create Intervention Summary page 162.

Shown in Intervention Summary page 162 is detail area 166. Upon selection of one of intervention codes 164, a detailed description of the selected intervention code is provided in area 166. The detailed description is obtained from web server database 51. As described above, the interventions listed in page 162 are intended to address a risk situation indicated by the notification selected in Notification Type page 109. Intervention Summary page 162 also provides areas to indicate an amount of time required to complete an intervention, a current status of an intervention, and any current barrier to executing the intervention. Such information is delivered to web client service 54 and stored in web server database 51 upon selection of corresponding Update icon 167. As a result, upon a subsequent access of Intervention Summary page 162, the updated information is included in Intervention Summary page 162 and delivered to web browser 88.

Figure 33:
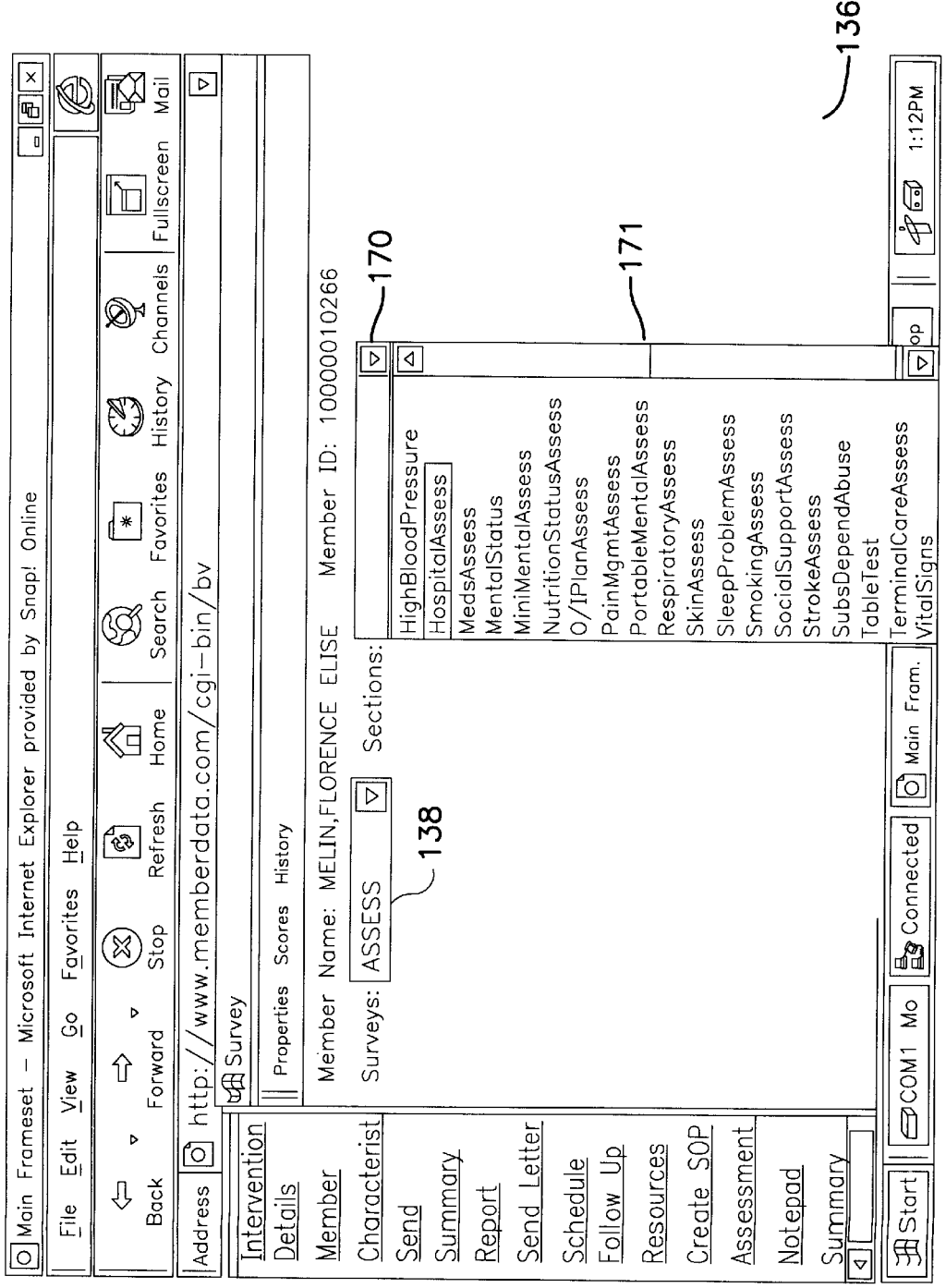
FIG. 33 is a view of a World Wide Web browser display and a java applet window in accordance with the present invention.

Intervention Summary page 162 lists several assessments among interventions to be performed. Such assessments are performed by selecting "Assessments" 135 from Coordination Plan frame 126. As described above, such a selection produces java applet window 136. As shown in FIG. 33, "Assess" is selected in Surveys field 138. Accordingly, Sections field 170 is displayed by the java applet, through which several assessments, shown in pull-down window 171, can be selected. If "HospitalAssess" is selected, as shown, the java applet requests a "Hospitalization" assessment from java proxy application 62. As described above with respect to FIG. 25 and FIG. 26, either a new or an old assessment can be retrieved.

Figure 34:
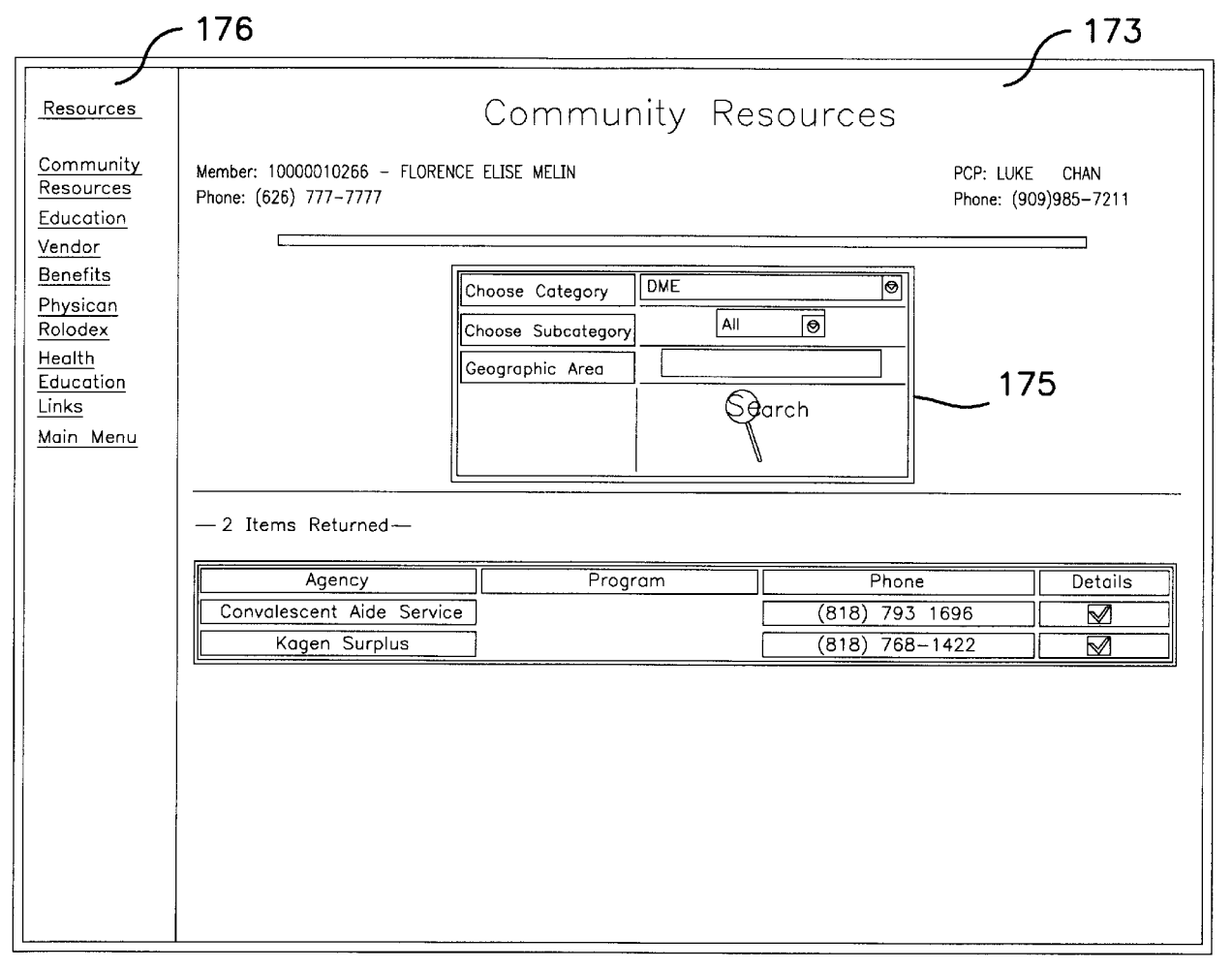

Intervention Summary page 162 also lists intervention 05A, for which community resources must be accessed. Accordingly, Coordination Plan frame 128 provides "Resources", through which Community Resources page 173 of FIG. 34 is accessed. Community resources, which are stored in web server database 51 according to category, sub-category and geographic area, can be searched using search table 175. In the illustrated instance, a search for Durable Medical Equipment providers performed by web client service 54 located two items from web server database 51 and inserted those items in a Community Resources page template and delivered the constructed page to web browser 88. As shown in Resources frame 176, other substantially static resource information is similarly accessible from web server database 51, such as information regarding member education, medical vendors, plan benefits, physician addresses and telephone numbers, and world wide web links to other health education.

Coordination Plan frame 128 also provides access to Send Letter frame 178, shown in FIG. 35. Send Letter frame 178 lists several letters corresponding to particular SOPs. Shown in FIG. 35 is a letter corresponding to SOP 1A1. Upon selection of "SOP 1A1", web client service 54 obtains demographic data from MPI 40 and completes an appropriate template from HTML templates 58 for transfer to web browser 88. The letter can thereafter be quickly printed via Generate Letter icon 180. Of course, a second option could be provided to automatically send the letter via facsimile to the member or to a provider using fax/modem interface 85.

Figure 36:
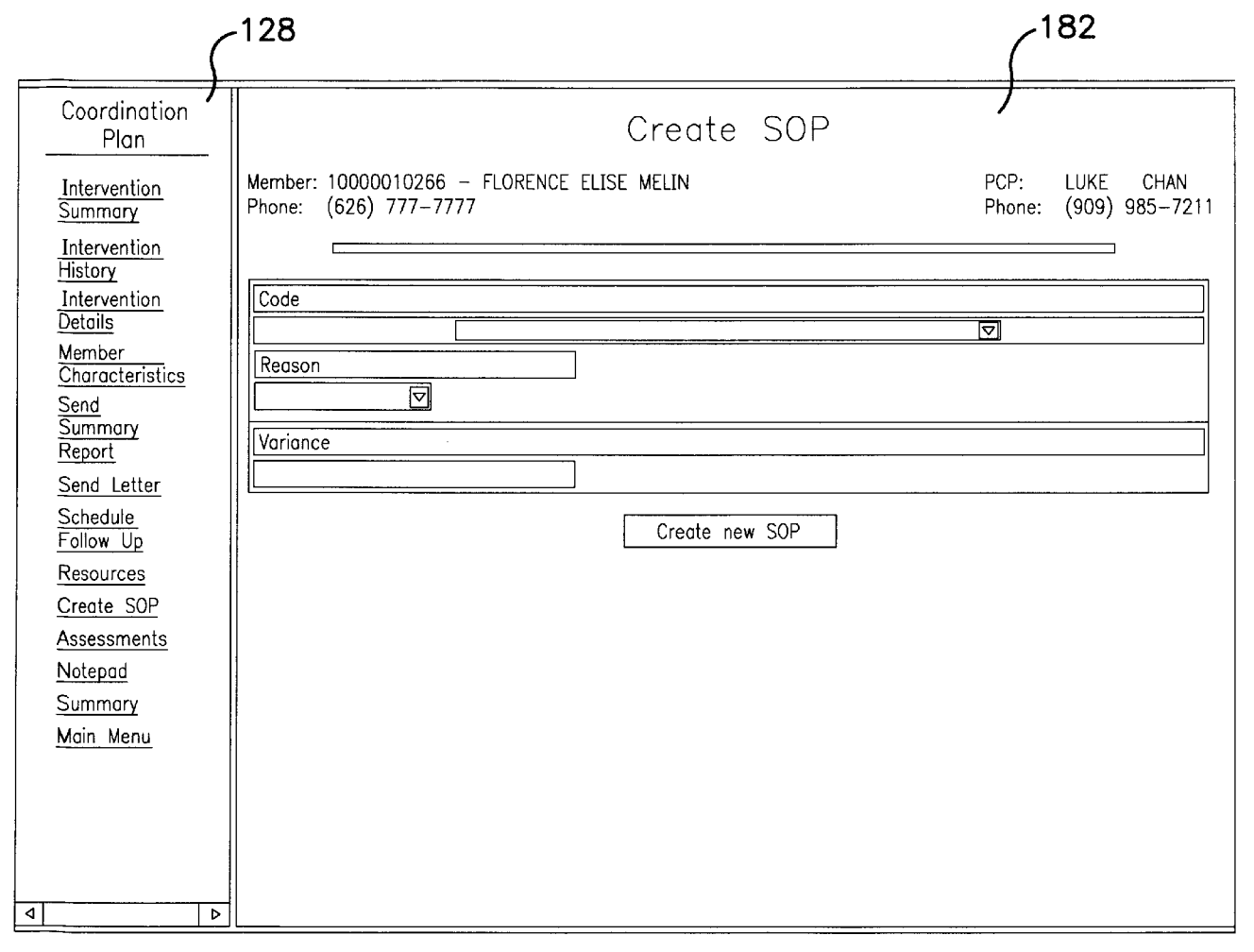

Coordination Plan frame 128 also lists "Create SOP", a selection of which results in display of Create SOP page 182, shown in FIG. 36. Page 182 enables a Coordination Specialist to define an SOP for storage in database 51. Preferably, the created SOP is stored in association with a particular intervention SOP or notification.

Figure 37:
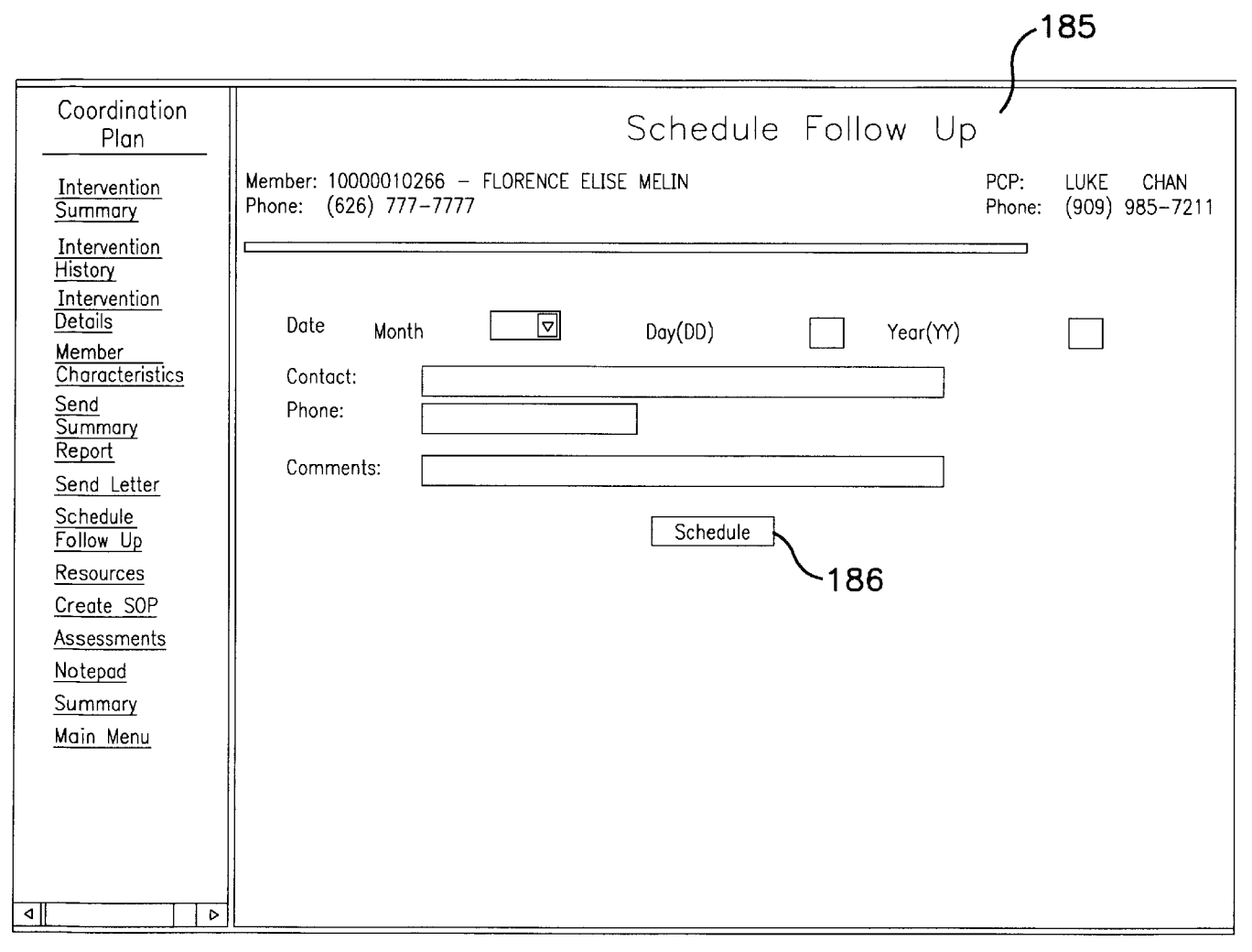

Schedule Follow-up page 185, shown in FIG. 37, is also accessible through Coordination Plan frame 128. A Coordination Specialist inputs a scheduled time into appropriate fields of page 185 and thereafter selects Schedule icon 186. As a result, at the scheduled time, a follow-up notification is added to the notification list stored in web server database 51. Accordingly, after the scheduled time, a follow-up notification corresponding to the scheduled follow-up is indicated in Main Menu page 106 at logon.

Main Menu frame 108 provides access to Transfer Member page 190, shown in FIG. 38. Using page 190, a member assigned to one Coordination Specialist may be transferred to another, or from one Coordination Specialist to a Case Manager. In response to such a transfer, the member is removed from the Coordination Specialist's member list stored in web server database 51 and added to the list of the Coordination Specialist or Case Manager to which the member is transferred. A notification is also triggered, which causes a member transfer notification to be displayed to the newly-responsible user upon logon.

As a result, any notifications corresponding to the transferred member will not appear to the original Coordination Specialist on display screen 66 upon logon, but will appear to the user to whom the member is transferred. An entry in Transfer Reason field 192 can be stored in web server database 51 as data for Notepad page 148 corresponding to the transferred member.

Problems and Goals page 194 is accessible through "Problems/Goals" 195 of Coordination Plan frame 128. As shown in FIG. 39, Problems and Goals page 194 displays problems which are determined based on an rule-based analysis of responses to assessments which have been completed or otherwise submitted to the system. Each problem is associated with at least one displayed goal. Associated with each goal are fields for specifying Target Goal, Target Date, current Goal Attainment, Date Met, and Status. Once a goal is indicated by a Coordination Specialist to be complete, the goal is displayed on Problems and Goals History page 196, shown in FIG. 40.

Problems and Goals History page 196 can be accessed via "Problems/Goals History" 200 of Coordination Plan frame 128. Page 196 displays those goals which have been designated as complete in Problems and Goals page 194. Page 196 also displays problems for which each associated goal has been designated as complete. As described with respect to Intervention History page 145, Problems and Goals History page 196 includes Undo buttons which cause goals listed on the page that day to be removed and returned to Problems and Goals page 194.

As also shown in FIG. 40, Coordination Plan frame 128 includes "Send Summary Report" option 202 for access to Summary Report page 205, shown in FIG. 41. Advantageously, web client service 54 creates Summary Report page 205 as described above using interaction manager 57, dynamic libraries 60, HTML templates 58, a member ID of the subject member, data repository 42, MPI 40, and data from web server database 51. More specifically, Summary Report page 205 summarizes problems and goals from member assessments, care coordination activities from interventions and comments, and may request physician intervention or feedback. Advantageously, such summary reports are also stored in web server database 51 in association with the member ID of the subject member to allow user access to previous summary reports via Summary Report page 205.

B. System Reports

The present invention also provides detailed reports for use by providers and/or a System Administrator. The invention enables generation of these reports by providing accessible storage of all data captured and generated in the system.

For care providers, useful reports include reports regarding member usage of specified medications or reports regarding follow-up care scheduled by the provider or a Coordination Specialist.

For a System Administrator, reports may be generated to monitor Coordination Specialist productivity. Such reports may, for example, document an average time elapsed between generation and deletion of a notification, along with corresponding Coordination Specialist and member identification information.

Other reports can be generated to monitor the caseload of the Coordination Specialists. Such reports may indicate how many interventions and how many assessments are performed on average per day.

Another type of report documents the number of members automatically assigned to a Coordination Specialist using received eligibility data, and the number not assigned due to an error in processing the received data. Similarly, a member transfer report can be generated to show when, from whom and to whom members have been transferred.

New enrollment can also be detected and reported periodically, along with a risk survey response rate corresponding to the newly-enrolled members. For new members not responding to a survey, demographic information may be printed for mailing of reminder letters.

A general overview of the patient population may be provided by a member characteristic report. In this regard, the member characteristic report lists member characteristics along with their frequency within the population.

Other types of system overviews can be obtained by reports containing combinations of the following information: the number of members requiring provider intervention, the number of members participating in disease management programs, the number of clinical alerts identified, all members having certain member characteristics, all members belonging to a specific health plan, etc.

It should be noted that the present invention allows generation of the foregoing types of reports by associatively storing all data used in the system and by providing a system to quickly and easily access the stored data.

C. Analytical Data Repository

The present invention also preferably includes an analytical data repository to provide system monitoring functions greater than those provided by the above-described reports. The analytical data repository contains copies of data stored in data repository 42, as well as other member-specific data stored in server database 51.

Data from the analytical data repository can be queried using database query language or subjected to statistical analysis using software programs. Advantageously, such operations do not interrupt system operation. Typical items to be analyzed include average care costs per month, average hospital stay per month, average number of hospital admissions per month, and average number of physician visits per month.

While the present invention is described above with respect to what is currently considered its preferred embodiments, it is to be understood that the invention is not limited to that described above. To the contrary, the invention is intended to cover various modifications and equivalent arrangements included within the spirit and scope of the appended claims.

What is claimed is:

1. A method for managing health care of a plurality of member patients in a population, comprising:

identifying member characteristics of one of the plurality of member patients;

storing a list of member characteristics of the one member patient in association with a corresponding medical data record of the one member patient;

continuously monitoring for input of member information indicative of a medical event corresponding to one of the plurality of member patients, the member information being input from one of a plurality of legacy health care systems;

obtaining member information indicative of a medical event corresponding to one of the plurality of member patients, the member information being input from one of a plurality of legacy health care systems;

translating the obtained member information to translated information having a predetermined format;

automatically identifying a risk situation associated with the one member patient from a list of potential risk situations, the potential risk situations being associated with one or more member characteristics and one or more medical events corresponding to the one member patient;

automatically generating a notification message corresponding to the risk situation, the notification message being associated with a predetermined script to address the identified risk situation;

automatically sending the notification message to a designated health care professional assigned to the one member patient; and updating the medical data record corresponding to the one member patient with an intervention plan input by the designated health care professional in response to the notification message.

2. A method according to claim 1, wherein the risk situation corresponds to a potential process failure in the delivery of health care to the member patient.

3. A method according to claim 1, wherein the member information is obtained from at least one of: lab data, claims data, pharmacy benefits manager data, home health care data, durable medical equipment provider data, health plan data, hospital admission data, physician encounter data, scheduling data, emergency room data, and case management data.

4. A method according to claim 1, wherein the member information is obtained from a network of health care-related entities.

5. A method according to claim 1, wherein the predetermined script includes at least one of: direction of the member patient to community resources, education of the member patient, assessment of the member patient's characteristics, automatic facsimile transmission of medical information to a caregiver, generation of a reminder letter, or physician paging.

6. A method according to claim 1, further comprising the steps of:

capturing intervention data; and updating member characteristics of the member patient based on the captured intervention data.

7. A method according to claim 1, wherein the notification message is associated with an instruction to update the list of member characteristics of the one member patient.

8. A method for storing health care-related information of a plurality of member patients, comprising:

receiving health care-related legacy source data from one of a plurality of legacy health care systems, the legacy source data corresponding to one of the member patients;

translating the legacy source data to translated data, the translated data having a common predetermined data format;

storing the translated data in association with a medical data record of the one member patient;

automatically determining whether the translated data correspond to one of a predetermined set of database triggers, each database trigger corresponding to a risk situation which is based on at least one member characteristic and at least one medical event;

automatically generating a notification message corresponding to a risk situation and storing a sequence number corresponding to the translated data, in a case that it is determined that the translated data correspond to one of the database triggers; and updating the medical data record of the one member patient with an intervention plan input by a designated health care professional in response to the notification message.

9. A computer-readable medium storing computer-executable process steps to manage health care of a plurality of member patients in a population, the process steps comprising:

an identifying step to identify member characteristics of one of the plurality of member patients;

a storing step to store a list of member characteristics of the one member patient in association with a corresponding medical data record of the one member patient;

a monitoring step to continuously monitor for input of member information indicative of a medical event corresponding to one of the plurality of member patients, the member information being input from one of a plurality of legacy health care systems;

an obtaining step to obtain member information indicative of a medical event corresponding to one of the plurality of member patients, the member information being input from one of a plurality of legacy health care systems;

translating the obtained member information to translated information having a predetermined format;

an identifying step to automatically identify a risk situation associated with the one member patient from a list of potential risk situations, the potential risk situations being associated with one or more member characteristics and one or more medical events corresponding to the one member patient;

a generating step to automatically generate a notification message corresponding to the risk situation, the notification message being associated with a predetermined script to address the identified risk situation;

a sending step to automatically send the notification message to a designated health care professional assigned to the one member patient; and an updating step to update the medical data record corresponding to the one member patient with an intervention plan input by the designated health care professional in response to the notification message.

10. A computer-readable medium according to claim 9, wherein the risk situation corresponds to a potential process failure in the delivery of health care to the member patient.

11. A computer-readable medium according to claim 9, wherein the member information is obtained from at least one of: lab data, claims data, pharmacy benefits manager data, home health care data, durable medical equipment provider data, health plan data, hospital admission data, physician encounter data, scheduling data, emergency room data, and case management data.

12. A computer-readable medium according to claim 9, wherein the member information is obtained from a network of health care-related entities.

13. A computer-readable medium according to claim 9, wherein the predetermined script includes at least one of: direction of the member patient to community resources, education of the member patient, assessment of the member patient's characteristics, automatic facsimile transmission of medical information to a caregiver, generation of a reminder letter, or physician paging.

14. A computer-readable medium according to claim 9, the process steps further comprising:
  a capturing step to capture intervention data; and
  an updating step to update member characteristics of the member patient based on the captured intervention data.

15. A computer-readable medium according to claim 9, wherein the notification message is associated with an instruction to update the list of member characteristics of the one member patient.

16. A computer-readable medium storing computer-executable process steps to store health care-related information of a plurality of member patients, the process steps comprising:
  a receiving step to receive health care-related legacy source data from one of a plurality of legacy health care systems, the legacy source data corresponding to one of the member patients;
  a translating step to translate the legacy source data to translated data, the translated data having a common predetermined data format;
  a storing step to store the translated data in association with a medical data record of the one member patient;
  a determining step to automatically determine whether the translated data correspond to one of a predetermined set of database triggers, each database trigger corresponding to a risk situation which is based on at least one member characteristic and at least one medical event;
  a generating step to automatically generate a notification message corresponding to a risk situation and to store a sequence number corresponding to the translated data in a case that it is determined that the translated data correspond to one of the database triggers; and
  updating the medical data record of the one member patient with an intervention plan input by a designated health care professional in response to the notification message.

17. A computer apparatus comprising:
  a memory for storing computer-executable process steps; and
  a processor for executing the computer-executable process steps stored in said memory to 1) identify member characteristics of one of a plurality of member patients, 2) store a list of member characteristics of the one member patient in association with a corresponding medical data record of the one member patient, 3) continuously monitor for input of member information indicative of a medical event corresponding to one of the plurality of member patients, the member information being input from one of a plurality of legacy health care systems, 4) obtain member information indicative of a medical event corresponding to one of the plurality of member patients, the member information being input from one of a plurality of legacy health care systems, 5) translating the obtained member information to translated information having a predetermined format, 6) automatically identify a risk situation associated with the one member patient from a list of potential risk situations, the potential risk situations being associated with one or more member characteristics and one or more medical events corresponding to the one member patient, 7) automatically generate a notification message corresponding to the risk situation, the notification message being associated with a predetermined script to address the identified risk situation, 8) automatically send the notification message to a designated health care professional assigned to the one member patient, and 9) update the medical data record corresponding to the one member patient with an intervention plan input by the designated health care professional in response to the notification message.

18. An apparatus according to claim 17, wherein the risk situation corresponds to a potential process failure in the delivery of health care to the member patient.

19. An apparatus according to claim 17, wherein the member information is obtained from at least one of: lab data, claims data, pharmacy benefits manager data, home health care data, durable medical equipment provider data, health plan data, hospital admission data, physician encounter data, scheduling data, emergency room data, and case management data.

20. An apparatus according to claim 17, wherein the member information is obtained from a network of health care-related entities.

21. An apparatus according to claim 17, wherein the predetermined script includes at least one of: direction of the member patient to community resources, education of the member patient, assessment of the member patient's characteristics, automatic facsimile transmission of medical information to a caregiver, generation of a reminder letter, or physician paging.

22. A apparatus according to claim 17, the processor for executing the computer-executable process steps stored in said memory to 10) capture intervention data, and 11) update member characteristics of the member patient based on the captured intervention data.

23. An apparatus according to claim 17, wherein the notification message is associated with an instruction to update the list of member characteristics of the one member patient.

24. A computer apparatus comprising:
  a memory for storing computer-executable process steps; and
  a processor for executing the computer-executable process steps stored in said memory to 1) receive health care-related legacy source data from one of a plurality of legacy health care systems, the legacy source data corresponding to one of the member patients, 2) translate the legacy source data to translated data, the translated data having a common predetermined data format, 3) store the translated data in association with a medical data record of the one member patient, 4) automatically determine whether the translated data correspond to one of a predetermined set of database triggers, each database trigger corresponding to a risk situation which is based on at least one member characteristic and at least one medical event, 5) automatically generate a notification message corresponding to a risk situation and store a sequence number corresponding to the translated data in a case that it is determined that the translated data correspond to one of the database triggers; and 6) update the medical data record of the one member patient with an intervention plan input by a designated health care professional in response to the notification message.

* * * * *

UNITED STATES PATENT AND TRADEMARK OFFICE
CERTIFICATE OF CORRECTION

PATENT NO.    : 6,385,589 B1                                              Page 1 of 1
DATED         : May 7, 2002
INVENTOR(S)   : Mark Trusheim et al.

It is certified that error appears in the above-identified patent and that said Letters Patent is hereby corrected as shown below:

<u>Title page,</u>
Item [56], References Cited, FOREIGN PATENT DOCUMENTS, insert
-- WO  97/28445      8/1997 --.

Insert
                       -- OTHER PUBLICATIONS
Margaret J. Gunther, "Measure, Monitor, and Manage" Health Management Technology, Sept. 2000, Vol. 21, No. 9, pp. 26-28. --

<u>Column 2,</u>
Line 31, change "rehabilation" to -- rehabilitation --.

<u>Column 3,</u>
Line 15, change "as-proactive" to -- as proactive --.

<u>Column 16,</u>
Line 32, change "obtained-from" to -- obtained from --.

<u>Column 17,</u>
Line 56, change "-resources" to -- resources --.

Signed and Sealed this

Fourth Day of March, 2003

Attest:

Attesting Officer

JAMES E. ROGAN
*Director of the United States Patent and Trademark Office*